(12) United States Patent
Thompson et al.

(10) Patent No.: US 6,673,611 B2
(45) Date of Patent: Jan. 6, 2004

(54) NUCLEIC ACID MOLECULES WITH NOVEL CHEMICAL COMPOSITIONS CAPABLE OF MODULATING GENE EXPRESSION

(75) Inventors: James Thompson, Lafayette, CO (US); Leonid Beigelman, Longmont, CO (US); James McSwiggen, Boulder, CO (US); Alexander Karpeisky, Lafayette, CO (US); Laurent Bellon, Frederick, MD (US); Mark Reynolds, Pleasanton, CA (US); Michael Zwick, Madison, WI (US); Thale Jarvis, Boulder, CO (US); Tod Woolf, Sudbury, MA (US); Peter Haeberli, Berthoud, CO (US); Jasenka Matulic-Adamic, Boulder, CO (US)

(73) Assignee: Sirna Therapeutics, Inc., Boulder, CO (US)

( * ) Notice: Subject to any disclaimer, the term of this patent is extended or adjusted under 35 U.S.C. 154(b) by 0 days.

(21) Appl. No.: 09/866,316

(22) Filed: May 25, 2001

(65) Prior Publication Data

US 2002/0142980 A1 Oct. 3, 2002

Related U.S. Application Data

(63) Continuation-in-part of application No. 09/103,636, filed on Jun. 23, 1998.
(60) Provisional application No. 60/082,404, filed on Apr. 20, 1998.

(51) Int. Cl.$^7$ .......................... C12Q 1/68; C12P 19/34; C12N 15/63; C07H 21/02; C07H 21/04

(52) U.S. Cl. .................... 435/455; 435/6; 435/91.1; 435/366; 536/23.1; 536/24.5

(58) Field of Search ............... 435/6, 91.31, 91.1, 435/325, 366, 375, 455; 536/23.1, 24.31, 24.33, 24.5; 514/44

(56) References Cited

U.S. PATENT DOCUMENTS

| | | |
|---|---|---|
| 4,987,071 A | 1/1991 | Cech et al. |
| 5,013,830 A | 5/1991 | Ohtsuka et al. |
| 5,144,019 A | 9/1992 | Rossi et al. |
| 5,264,423 A | 11/1993 | Cohen et al. |
| 5,272,065 A | 12/1993 | Inouye et al. |
| 5,276,019 A | 1/1994 | Cohen et al. |
| 5,286,717 A | 2/1994 | Cohen et al. |
| 5,334,711 A | 8/1994 | Sproat et al. |
| 5,491,133 A | 2/1996 | Walder et al. |
| 5,525,468 A | 6/1996 | McSwiggen |
| 5,576,208 A | * 11/1996 | Monia et al. |
| 5,587,362 A | 12/1996 | Chu et al. |
| 5,623,065 A | 4/1997 | Cook et al. |
| 5,624,803 A | 4/1997 | Noonberg et al. |
| 5,625,047 A | 4/1997 | Been et al. |
| 5,627,053 A | 5/1997 | Usman et al. |
| 5,631,359 A | 5/1997 | Chowrira et al. |
| 5,633,133 A | 5/1997 | Long et al. |
| 5,652,094 A | 7/1997 | Usman et al. |
| 5,652,355 A | 7/1997 | Metelev et al. |
| 5,652,356 A | 7/1997 | Agrawal |
| 5,678,731 A | 10/1997 | Okamura et al. |
| 5,716,824 A | 2/1998 | Beigelman et al. |
| 5,849,902 A | 12/1998 | Arrow et al. |
| 5,919,619 A | 7/1999 | Tullis |
| 5,989,912 A | 11/1999 | Arrow et al. |
| 5,998,203 A | * 12/1999 | Matulic-Adamic et al. |
| 6,001,311 A | 12/1999 | Brennan |
| 6,001,653 A | 12/1999 | Crooke et al. |
| 6,159,714 A | 12/2000 | Usman et al. |

FOREIGN PATENT DOCUMENTS

| | | |
|---|---|---|
| EP | 0 360 257 A2 | 3/1990 |
| WO | 89/02439 | 3/1989 |
| WO | 91/03162 | 3/1991 |
| WO | 92/07065 | 4/1992 |
| WO | 93/15187 | 8/1993 |
| WO | 93/23569 | 11/1993 |
| WO | 94/02595 | 2/1994 |
| WO | 95/11910 | 5/1995 |
| WO | 96/10390 | 4/1996 |
| WO | 96/10391 | 4/1996 |
| WO | 96/10392 | 4/1996 |
| WO | 96/17086 | 6/1996 |
| WO | 96/18736 | 6/1996 |
| WO | 96/19577 | 6/1996 |
| WO | 97/26270 | 7/1997 |
| WO | 98/13526 | 4/1998 |
| WO | 99/05094 | 7/1998 |
| WO | 98/58058 | 12/1998 |
| WO | 99/04819 | 2/1999 |
| WO | 99/16871 | 4/1999 |
| WO | 99/55857 | 4/1999 |
| WO | 99/54459 | 10/1999 |

OTHER PUBLICATIONS

Jen et al., Stem Cells, vol. 18, pp. 307–319, 2000.*
Green et al. J. of Am. Coll. Surg. vol. 191, No. 1, Jul. 2000.*
Agrawal et al. Molecular Medicine Today, vol. 6, pp. 72–81, Feb. 2000.*
Ma et al., Biotechnology Annula Review, vol. 5, pp. 155–196, 2000.*
Branch, TIBS 23, pp. 45–50, Feb. 1998.*
Flanagan et al., Nature Biotechnology, vol. 17, No. 1, pp. 48–52, Jan. 1999.*
Bennett et al. "Pharmacology of Antisense Therapeutic Agents", Chapter 2, from Methods in Molecular Medicine: Antisense Therapeutics, Ed. S. Agrawal, Humana Press Inc., Totowa, NJ, ISBN: 0_89603–305–8, 1996.*

(List continued on next page.)

*Primary Examiner*—Ram R. Shukla
*Assistant Examiner*—Jane Zara
(74) *Attorney, Agent, or Firm*—McDonnell Boehnen Hulbert & Berghoff

(57) ABSTRACT

This invention relates to novel chemically-modified nucleic acid molecules having specific formulae that exhibit increased resistance to nucleases and increased binding affinity to target nucleic acid molecules. The invention further relates to methods of modulating gene expression using the novel chemically modified nucleic acid molecules, and compositions and cells comprising said molecules.

17 Claims, 4 Drawing Sheets

OTHER PUBLICATIONS

Abramovitz et al., "Catalytic Role of 2'–Hydroxyl Groups Within a Group II Intron Active Site," *Science* 271:1410–1413 (1996).

Agrawal et al., "Site–specific excision from RNA by Rnase H and mixed–phosphate–backbone oligodeoxynucleotides," *Proc. Natl. Acad. Sci. USA* 87:1401–1405 (1990).

Akhtar and Juliano, "Cellular uptake and intracellular fate of antisense oligonucleotides," *Trends in Cell Biology* 2:139–144 (1992).

Aldrian–Herrada et al., "A peptide nucleic acid (PNA) is more rapidly internalized in cultured neurons when coupled to a retro–inverso delivery peptide. The antisense activity depresses the target mRNA and protein in magnocellular oxytocin neurons," *Nucleic Acids Research* 26:4910–4916 (1998).

Altmann et al., "Second generation of antisense oligonucleotides: From nuclease resistance to biological efficacy in animals," *Chimia* 50:168–176 (1996).

Ashley, "Modeling, Synthesis, and Hybridization Properties of (L)–Ribonucleic Acid," *J. Am. Chem Soc.* 114:9731–9736 (1992).

Banerjee and Turner, "The Time Dependence of Chemical Modification Reveals Slow Steps in the Folding of a Group I Ribozyme," *Biochemistry* 34:6504–6512 (1995).

Bartel and Szostak, "Isolation of New Ribozymes From a Large Pool of Random Sequences," *Science* 261:1411–1418 (1993).

Beaucage et al., "The functionalization of oligonucleotides via phosphoramidite derivatives," *Tetrahedron* 49:1925–1963 (1993).

Beaudry et al., "Directed Evolution of an RNA Enzyme," *Science* 257:635–641 (1992).

Beigelman et al., "Chemical Modification of Hammerhead Ribozymes," *J. Biol. Chem.* 270:25702–25708 (1995).

Bellon et al., "Amino–Linked Ribozymes: Post–Synthetic Conjugation of Half–Ribozymes," *Nucleosides & Nucleotides* 16:951–954 (1997).

Bellon et al., "Post–synthetically Ligated Ribozymes: An Alternative Aproach to Iterative Solid–Phase Synthesis," *Bioconjugate Chem.* 8:204–212 (1997).

Berzal–Herranz et al., "Essential nucleotide sequences and secondary structure elements of the hairpin ribozyme," *EBMO J.* 12:2567–2574 (1993).

Berzal–Herranz et al., "In vitro selection of active hairpin ribozymes by sequential RNA–catalyzed clevage and ligation reactions," *Genes & Development* 6:129–134 (1992).

Bevilacqua et al., "A Mechanistic Framework for the Second Step of Splicing Catalyzed by the Tetrahymena Ribozyme," *Biochemistry* 35:648–658 (1996).

Boado, "Antisense drug delivery through the blood–brain barrier," *Advanced Drug Delivery Reviews* 15:73–107 (1995).

Boado et al., "Drug Delivery of Antisense Molecules to the Brain for Treatment of Alzheimer's Disease and Cerebral AIDS," *Journal of Pharmaceutical Sciences* 87:1308–1315 (1998).

Borras et al., "Estradiol–induced Down–regulation of Estrogen Receptor. Effect of Various Modulators of Protein Synthesis and Expression," *J. Steroid Biochem. Molec. Biol.* 48:325–336 (1994).

Borras et al., "Estrogenic and Antiestrogenic Regulation of the Half–life of Covalently Labeled Estrogen Receptor in MCF–7 Breast Cancer Cells," *J. Steroid Biochem. Molec. Biol.* 57:203–213 (1996).

Breaker, "Catalytic DNA: in training and seeking employment," *Nature Biotechnology* 17:422–423 (1999).

Breaker et al., "A DNA enzyme with $Mg^{2}$–dependent RNA phosphoesterase activity," *Chemistry & Biology* 2(10):655–660 (1995).

Breaker and Joyce, "Inventing and improving ribozyme function: rational design versus iterative selection methods," *TIBTECH* 12:268–275 (1994).

Breaker, "Are engineered proteins getting competition from RNA?" *Current Opinion in Biotechnology* 7:442–448 (1996).

Brennan et al., "Two–Dimensional Parallel Array Technology as a New Approach to Automated Combinatorial Solid–Phase Organic Synthesis," *Biotechnology and Bioendineering (Combinatorial Chemistry)* 61:33–45 (1998).

Burgin et al., "Chemically Modified Hammerhead Ribozymes with Improved Catalytic Rates," *Biochemistry* 35:14090–14097 (1997) (vol. No. mistakenly listed as 6).

Burke et al., "Structural Analysis and Modifications of the Hairpin Ribozyme," *Nucleic Acids and Molecular Biology*, edited by Eckstein and Lilley, Springer–Verlag Berlin Heidelberg, 10:129–143 (1996).

Burlina et al., "chemical Engineering of Rnase Resistant and Catalytically Active Hammerhead Ribozymes," *Bioorganic & Medicinal Chemistry* 5:1999–2010 (1997).

Cao and Matteucci, "Preparation, Characterization and Binding Properties of an Oligodeoxynucleotide Containing the 3'–Ribothiofarmacetal Phosphate Analog," *Bioorganic & Medicinal Chemistry Letters* 4:807–810 (1994).

Caruthers et al., "Chemical Synthesis of Deoxyoligonucleotides and Deoxyoligonucleotide Analogs," *Methods in Enzymology* 211:3–19 (1992).

Cech et al., "Representation of the secondary and tertiary structure of group I introns," *structural biology* 1:273–280 (1994).

Cech, "Ribozymes and Their Medical Implications," *JAMA* 260:3030–3034 (1988).

Chartrand et al., "An oligodeoxyribonucleotide that supports catalytic activity in the hammerhead ribozyme domain," *Nucleic Acids Research* 23(20):4092–4096 (1995).

Chen et al., "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates," *Nucleic Acids Research* 20:4581–4589 (1992).

Chowrira et al., "In Vitro and in Vivo Comparison of Hammerhead, Hairpin, and Hepatitis Delta Virus Self–Processing Ribozyme Cassettes," *J. Biol. Chem.* 269:25856–25864 (1994).

Chowrira et al., "Novel guanosine requirement for catalysis by the hairpin ribozyme," *Nature* 354:320–322 (1991).

Christoffersen and Marr, "Riobozymes as Human Therapeutic Agents," *J. Med. Chem.* 38:2023–2037 (1995) (also referred to as Christofferson and Marr).

Christoffersen, "Translating genomics information into therapeutics: A Key Role for Oligonucleotides," *Nature Biotechnology* 15:483–484 (1997) (Christofferson).

Christofferson et al., "Application of computational technologies to ribozyme biotechnology products," *Journal of Molecular Structure (Theochem)* 311:273–284 (1994) (Christoffersen).

Cload and Schepartz, "Polyether Tethered Oligonucleotide Probes," *J. Am. Chem. Soc.* 113:6324–6326 (1991).

Cook et al., "The Use of Antisense Oligonucleotides to Establish Autocrine Angiotensin Growth Effects in Human Nueroblastoma and Mesangial Cells," *Antisense Research and Development* 2:199–210 (1992).

Cosstick et al, "Synthesis and properties of dithymidine phosphate analogues containing 3'–thiothymidine," *Nucleic Acids Research* 18:829–835 (1990).

Couture and Stinchcomb, "Anti–gene therapy: the use of ribozymes to inhibit the gene function," *Trends In Genetics* 12:510–515 (1996).

Crooke et al., "Kinetic characteristics of *Escherichia coli* Rnase H1: Cleavage of various antisense oligonucleotide–RNA duplexes," *Biochem. J.* 312:599–608 (1995).

Crooke, "Progress in Antisense Technology: The End of the Beginning," *Methods in Enzymology* 313:3–45 (1999).

Crooke, "Progress in Antisense Therapeutics," *Medicinal Research Reviews* 16:319–344 (1996).

Crooke, "Advances in Understanding the Pharmacological Properties of Antisense Oligonucleotides," *Advances in Pharmacology* 40:1–49 (1997).

Crooke, "Antisense Therapeutics," *Biotechnology and Genetic Engineering Reviews* 15:121–157 (1998).

Daniels et al., "Two Competing Pathways for Self–splicing by Group II Introns: A Quantitative Analysis of in Vitro Reaction Rates and Products," *J. Mol. Biol.* 256:31–49 (1996).

deFazio et al., "Antisense Estrogen Receptor RNA Expression Increases Epidermal Growth Factor Receptor Gene Expression in Breast Cancer Cells," *Cell Growth & Differentiation* 8:903–911 (1997).

Delihas et al., "Natural antisense RNA/target RNA interactions: Possible models for antisense oligonucleotide drug design," *Nature Biotechnology* 15:751–753 (1997).

Dreyfus, "Restriction Ribozymes?" *Einstein Quarterly Journal of Biology and Medicine* 6:92–93 (1988).

Dropulic et al., "Functional Characterization of a U5 Ribozyme: Intracellular Suppression of Human Immunodeficiency Virus Type I Expression," *Journal of Virology* 66:1432–1441 (1992).

Durand et al., "Circular Dichroism Studies of an Oligodeoxyribonucleotide Containing a Hairpin Loop Made of a Hexaethylene Glycol Chain: Conformation and Stability," *Nucleic Acids Research* 18:6353–6359 (1990).

Duval–Valentin, "Specific inhibition of transcription by triple helix–forming oligonucleotides," *Proc. Natl. Acad. Sci. USA* 89:504–508 (1992).

Earnshaw et al., "Modified Oligoribonucleotides as Site–Specific Probes of RNA Structure and Function," *Biopolymers* 48:39–55 (1998).

Egholm et al., "PNA hybridizes to complementary oligonucleotides obeying the Watson–Crick hydrogen–bonding rules," *Nature* 365:566–568 (1993).

Elroy–Stein and Moss, "Cytoplasmic Expression System Based on Constitutive Synthesis of Bacteriophage T7 RNA Polymerase in Mammalian Cells," *Proc. Natl. Acad. Sci. USA* 87:6743–6747 (1990).

Emerich et al., "Biocompatability of Poly (DL–Lactide–co–Glycolide) Microsheres Implanted Into the Brain," *Cell Transplantation* 8:47–58 (1999).

Ferentz and Verdine, "Disulfied Cross–Linked Oligonucleotides," *J. Am. Chem. Soc.* 113:4000–4002 (1991).

Forster and Altman, "External Guide Sequences for an RNA Enzyme," *Science* 249:783–786 (1990).

Fox, "Targeting DNA with Triplexes," *Current Medicinal Chemistry* 7:17–37 (2000).

Freier et al., "Improved free–energy parameters for predictions of RNA duplex stability," *Proc. Natl. Acad. Sci. USA* 83:9373–9377 (1986).

Gao and Huang, "Cytoplasmic Expression of a Reporter Gene by Co–Delivery of T7 RNA Polymerase and T7 Promoter Sequence with Cationic Liposomes," *Nucleic Acids Research* 21:2867–2872 (1993).

Gold, "Axonal Regeneration of Sensory Nerves is Delayed by Continuous Intrathecal Infusion of Nerve Growth Factor," *Neuroscience* 76:1153–1158 (1997).

Good et al., "Expression of small, therapeutic RNAs in human nuclei," *Gene Therapy* 4:45–54 (1997).

Grasby et al., "Purine Functional Groups in Essential Residues of the Hairpin Ribozyme Required for Catalytic Cleavage of RNA," *Biochemistry* 34:4068–4076 (1995).

Green et al., "Human oestrogen receptor cDNA: sequence, expression and homology to v–erb–A," *Nature* 320:134–139 (1986).

Griffin et al., "Group II intron ribozymes that cleave DNA and RNA linkages with similar efficiency, and lack contacts with substrate 2'–hydroxyl groups," *Chemistry & Biology* 2:761–770 (1995).

Groothius et al., "The entry of antiviral and antiretroviral drugs into the central nervous system," J. NeuroVirol 3:387–400 (1997).

Guo and Collins, "Efficient trans–cleavage of a stem–loop RNA substrate by a ribozyme derived from Neurospora VS RNA," *EMBO J.* 14:368–376 (1995).

Hammann et al., "Length Variation of Helix III in a Hammerhead Ribozyme and Its Influence on Cleavage Activity," *Antisense & Nucleic Acid Drug Development* 9:25–31 (1999).

Hampel et al., "'Hairpin' Catalytic RNA Model: Evidence for Helices and Sequence Requirement for Substrate RNA," *Nucleic Acids Research* 18:299–304 (1990).

Harris et al., "Identification of phosphates involved in catalysis by the ribozyme RNase P RNA," *RNA* 1:210–218 (1995).

Haseloff and Gerlach, "Simple RNA Enzymes with New and Highly Specific Endoribonuclease Activities," *Nature* 334:585–591 (1988).

Hegg et al., "Kinetics and Thermodynamics of Intermolecular Catalysis by Hairpin Ribozymes," *Biochemistry* 34:15813–15828 (1995).

Henningfeld et al., "Alteration of DNA Primary Structure by DNA Topoisomerase I. Isolation of the Covalent Topoisomerase I–DNA Binary Complex in Enzymatically Competent Form," *J. Am. Chem. Soc.* 118:11701–11714 (1996).

Herschlag and Cech, "Catalysis of RNA Cleavage by the *Tetrahymena thermophila* Ribozyme 1. Kinetic Description of the Reaction of an RNA Substrate Complementary to the Active Site," *Biochemistry* 29:10159–10171 (1990).

Herschlag and Cech, "Catalysis of RNA Cleavage by the *Tetrahymena thermophila* Ribozyme. 2. Kinetic Description of the Reaction of an RNA Substrate That Forms a Mismatch at the Active Site," *Biochemistry* 29:10172–10180 (1990).

Hertel et al., "A Kinetic Thermodynamic Framework for the Hammerhead Ribozyme Reaction," *Biochemistry* 33:3374–3385 (1994).

Hertel et al., "Numbering System for the Hammerhead," *Nucleic Acids Research* 20:3252 (1992).

Higson et al., "Synthesis and Structure of S–Nucleosidyl S–Aryl Disulfides and their Reaction with Phosphites," *Tetrahedron* 52:1027–1034 (1996).

Hostomsky et al., "Ch. 11—Ribonucleases H," in *Nucleases*, edited by Linn et al., Cold Spring Harbor Laboratory Press, NY, pp. 341–376 (1993).

Inoue et al., Sequence–dependent hydrolysis of RNA using modified oligonucleotide splints and RNase H,; *FEBS Letters* 215:327–330 (1987).

Inoue et al., "Synthesis and hybridization studies on two complementary nona(2'–O–methyl) ribonucleotides," *Nucleic Acids Research* 15:6131–6149 (1987).

Ishiwata et al., "Physical–Chemistry Characteristics and Biodistribution of Poly(ethylene glycol)–Coated Liposomes Using Poly(oxyethylene) Cholesteryl Ether," *Chem. Pharm. Bull.* 43:1005–1011 (1995) (mistakenly referred to as Ishiwataet).

Izant and Weintraub, "Constitutive and Conditional Suppression of Exogenous and Endogeneous Genes by Anti–Sense RNA," *Science* 229:345–352 (1985).

Jaeger et al., "Improved Predictions and Secondary Structures for RNA," *Proc. Natl. Acad. Sci. USA* 86:7706–7710 (1989).

Jankowsky et al., "Peptide nucleic acid (PNA) is capable of enhancing hammerhead ribozyme activity with long but not with short RNA substrates," *Nucleic Acids Research* 25:2690–2693 (1997).

Jaschke et al., "Automated Incorporation of Polyethylene Glycol into Synthetic Oligonucleotides," *Tetrahedron Letters* 34:301–304 (1993).

Jeffries and Symons, "A Catalytic 13–mer Ribozyme," *Nucleic Acids Research* 17:1371–1377 (1989) (also referred to as Jefferies).

Jiang et al., "Growth Regulation of Estrogen Receptor–Negative Breast Cancer Cells Transfected with Complementary DNAs for Estrogen Receptor," *J. Natl. Cancer Inst.* 84:580–591 (1992).

Jolliet–Riant and Tillement, "Drug transfer acorss the blood–brain barrier and improvement of brain delivery," *Fundam. Clin. Pharmacol.* 13:16–26 (1999).

Jordan et al., "Endocrine Pharmacology of Antiestrogens and Antitumor Agents," *Endocrine Reviews* 11:578–610 (1990).

Joseph et al., "Substrate selection rules for the hairpin ribozyme determined by in vitro selection, mutation, and analysis of mismatched substrates," *Genes & Development* 7:130–138 (1993).

Joyce et al., "Amplification, mutation and selection of catalytic RNA," *Gene* 82:83–87 (1989).

Joyce, "Directed Molecular Evolution," *Scientific American* 267:90–97 (1992).

Karpeisky et al, "Highly Efficient Synthesis of 2'–O–Amino Nucleosides And Their Incorporation in Hammerhead Ribozymes," *Tetrahedron Letters* 39:1131–1134 (1998).

Kashani–Sabet et al., "Reversal of the Malignant Phenotype by an Anti–ras Ribozyme," *Antisense Research & Development* 2:3–15 (1992).

Karpeisky et al, "2'–O–Methylthiomethyl Modifications In Hammerhead Ribozymes," *Nucleosides & Nucleotides* 16(7–9):955–958 (1997).

Kim and Cech, "Three–dimensional model of the active site of the self–splicing rRNA precursor of Tetrahymena," *Proc. Natl. Acad. Sci. USA* 84:8788–8792 (1987).

Kim et al., "Inhibition of Transcription of the Human c–myc Protooncogene by Intermolecular Triplex," *Biochemistry* 37:2299–2304 (1998).

Klubmann et al., "Mirror–image RNA that binds D–adenosine," *Nature Biotechnology* 14:1112–1115 (1996).

Knitt et al., "ph Dependencies of the Tetrahymena Ribozyme Reveal an Unconvential Origin of an Apparent $pK_a$," *Biochemistry* 35:1560–1570 (1996).

Kore et al., "Sequence specificity of the hammerhead ribozyme revisistsed; the NIH rule", *Nucleic Acids Research*, 26(18):4116–4120 (1998).

Kumar and Ellington, "Artificial evolution of natural ribozymes," *FABEB J.* 9:1183–1195 (1995).

Lasic and Papahadjopoulos, "Liposomes Revisited," *Science* 267:1275–1276 (1995).

Lasic and Needham, "The 'Stealth' Liposome: A Prototypical Biomaterial," *Chemical Reviews* 95:2601–2627 (1995).

Lehmann et al., "Solid–phase synthesis of oligoribonucleotides using 9–fluoroenylmethoxycarbonyl (Fmoc) for 5'–hydroxyl protection," *Nucleic Acids Research* 17:2379–2390 (1989).

L'Huillier et al., "Cytoplasmic Delivery of Ribozymes Leads to Efficient Reduction in α–Lactalbumin mRNA Levels in C1271 Mouse," *EMBO J.* 11:4411–4418 (1992).

Li et al., "Thermodynamic and Activation Parameters for Binding of a Pyrene–Labeled Substrate by the Tetrahymena Ribozyme: Docking is Not Diffusion–Controlled and is Driven by a Favorable Entropy Change," *Biochemistry* 34:14394–14399 (1995).

Li et al., "Application of the Michaelis–Arbusov Reaction to the Synthesis of Internucleoside 3'–S–Phosphorothiolate Linkages," *J. Chem. Soc. Perkin Trans. I*, 15:2123–2129 (1994).

Li et al., "Synthesis of a Dinucleoside 3'–S–Phosphorothiolate Containing 2'–Deoxy–3'–Thioadenosine," *Tetrahedron* 48:2729–2738 (1992).

Lieber et al., "Stable High–Level Gene Expression in Mammalian Cells by T7 Phage RNA Polymerase," *Methods Enzymol.* 217:47–66 (1993).

Limbach et al., "Summary: the modified nucleosides of RNA," *Nucleic Acids Research* 22(12):2183–2196 (1994).

Lisacek et al., "Automatic Identification of Group I Intron Cores in Genomic DNA Sequences," *J. Mol. Biol.* 235:1206–1217 (1994).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

Liu et al., "3'–Thiouridylyl–(3'→5')–uridine," *Tetrahedron Letters* 37:925–928 (1996).

Liu et al., "Cationic Liposome–mediated Intravenous Gene Delivery," *J. Biol. Chem.* 270(42):24864–24870 (1995).

Long and Uhlenbeck, "Kinetic characterization of intramolecular and intermolecular hammerhead RNAs with stem II deletions," *Proc. Natl. Acad. Sci. USA* 91:6977–6981 (1994).

Ma et al., "Design and Synthesis of RNA Miniduplexes via a Synthetic Linker Approach," *Biochemistry* 32:1751–1758 (1993).

Ma et al., "Design and Synthesis of RNA Miniduplexes via a Synthetic Linker Approach. 2. Generation of Covalently Closed, Double–Stranded Cyclic HIV–1 TAR RNA Analogs with High Tat–Binding Affinity," *Nucleic Acids Research* 21:2585–2589 (1993).

Matulic–Adamic et al., "Synthesis and Incorporation of 2'–Amino Acid Conjugated Nucleotides Into Ribozymes," *Bioorganic & Medicinal Chemistry Letters* 5:2721–2724 (1995).

Matulic–Adamic et al., "Synthesis and Incorporation of 5'–Amino– and 5'–Mercapto–5'Deoxy–2'–O–Methyl Nucleosides Into Hammerhead Ribozymes," *Nucleosides & Nucleotides* 16:1933–1950 (1997).

McCarthy et al., "Enduring Consequences of Neonatal Treatment with Antisense Oligodeoxynucleotides to Estrogen Receptor Messenger Ribonucleic Acid on Sexual Differentiation of Rat Brain," *Endocrinology* 133:433–439 (1993).

McCurdy et al., "Deoxyoligonucleotides with Inverted Polarity: Synthesis and Use in Triple–Helix Formation" *Nucleosides & Nucleotides* 29:287–290 (1991).

McGarry and Lindquist, "Inhibiting of heat shock protein synthesis by heat–inducible antisense RNA," *Proc. Natl. Acad. Sci. USA* 83:399–403 (1986).

McKay, "Structure and function of the hammerhead ribozyme: an unfinished story," *RNA* 2:395–403 (1996).

Mengel and Greisser, "Nucleophilic Displacement Reactions with Thiobenzoate. New Synthesis of Deoxy–Thioadenosine Derivatives Starting from Adenosine," *Tetrahedron Letters* 13:1177–1180 (1977).

Michel and Westhof, "Slippery substratrates," *Nat. Struct. Biol.* 1:5–7 (1994).

Michel et al., "Structure and Activities of Group II Introns," *Annu. Rev. Biochem.* 64:435–461 (1995).

Michels and Pyle, "Conversion of a Group II Intron into a New Multiple–Turnover Ribozyme that Selectively Cleaves Oligonucleotides: Elucidation of Reaction Mechanism and Structure/Function Relationships," *Biochemistry* 34:2965–2977 (1995).

Mitra et al., "A mammalian 2–5A system functions as an antiviral pathway in transgenic plants," *Proc. Natl. Acad. Sci. USA* 93:6780–6785 (1996).

Monia et al., "Evaluation of 2'–Modified Oligonucleotides Containing 2'–Deoxy Gaps as Antisense Inhibitors of Gene Expression," *J. Biol. Chem.* 268:14514–14522 (1993).

Moore and Sharp, "Site–Specific Modification of Pre–mRNA: The 2'–Hydroxyl Groups at the Splice Sites," *Science* 256:992–996 (1992).

Mukhopadhyay et al., "Antisense Regulation of Oncogenes in Human Cancer," *Critical Reviews in Oncogenesis* 7:151–190 (1996).

Nakamaye and Eckstein, "AUA–Cleaving Hammerhead Ribozymes: Attempted Selection for Improved Cleavage," *Biochemistry* 33:1271–1277 (1994).

Nathans and Smith, "Restriction Endonucleases in the Analysis and Restructuring of DNA Molecules," *Ann. Rev. Biochem.* 44:273–295 (1975).

Noonberg et al., In vivo generation of highly abundant sequence–specific oligonucleotides for antisense and triplex gene regulation, *Nucleic Acids Research* 22(14):2830–2836 (1994).

Ohkawa et al., "Activities of HIV–RNA Targeted Ribozymes Transcribed From a 'Shot Gun' Type Ribozyme–trimming Plasmid," *Nucleic Acids Symp. Ser.* 27:15–16 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Oku et al., "Real–time analysis of liposomal trafficking in tumor–bearing mice by use of positron emission tomography," *Biochimica et Biophysica Acta* 1238:86–90 (1995).

Ono et al., "DNA Triplex Formation of Oligonucleotide Analogues Consisting of Linker Groups and Octamer Segments That Have Opposite Sugar–Phosphate Backbone Polarities," *Biochemistry* 30:9914–9921 (1991).

Orgel, "Selection in vitro," *Proc. R. Soc. London B,* 205:435–442 (1979).

Pace and Smith, "Ribonuclease P: Function and Variation," *J. Biol. Chem.* 265:3587–3590 (1990).

Pan et al., "Probing of tertiary interactions in RNA: 2'–Hydroxyl–base contacts between the Rnase P and pre–tRNA," *Proc. Natl. Acad. Sci. USA* 92:12510–12514 (1995).

Pandey et al., "Role on B61, the Ligand for the Eck Receptor Tyrosine Kinase, in TFN–α–Induced Angiogenesis," *Science* 268:567–569 (1995).

Pardridge et al., "Vector–mediated delivery of a polyamide ("peptide") nucleic acid analogue through the blood–brain barrier in vivo," *Proc. Natl. Acad. Sci. USA* 92:5592–5596 (1995).

Perreault et al., "Mixed Deoxyribo– and Ribo–Oligonucleotides with Catalytic Activity," *Nature* 344:565–567 (1990) (often mistakenly listed as Perrault).

Perrotta and Been, "A pseudoknot–like structure required for efficeint self–cleavage of hepatitis delta virus RNA," *Nature* 350:434–436 (1991).

Perrotta and Been, "Cleavage of Oligoribonucleotides by a Ribozyme Derived from the Hepatitis δ Virus RNA Sequence," *Biochemistry* 31:16–21 (1992).

Pieken et al., "Kinetic Characterization of Ribonuclease–Resistant 2'–Modified Hammerhead Ribozymes," *Science* 253:314–317 (1991).

Pink and Jordan, "Models of Estrogen Receptor Regulation by Estrogens and Antiestrogens in Breast Cancer Cell Lines," *Cancer Research* 56:2321–2330 (1991).

Player and Torrence, "The 2–5 A System: Modulation of Viral and Cellular Processes Through Acceleration of RNA Degradation," *Pharmacol. Ther.* J78:55–113 (1998).

Potts et al., "Epithelial–mesenchymal transformation of embryonic cardiac endothelial cells is inhibited by a modified antisense oligodeoxynucleotide to transforming growth factor γ3," *Proc. Natl. Acad. Sci. USA* 88:1516–1520 (1991).

Praseuth et al., "Triple helix formation and the antigene for sequence–specific control of gene expression," *Biochimica et Biophysica Acta* 1489:181–206 (1999).

Puttaraju et al., "A circular trans–acting hepatitis delta virus ribozyme," *Nucleic Acids Research* 21:4253–4258 (1993).

Pyle et al., "Building a Kinetic Framework for Group II Intron Ribozyme Activity: Quantitation of Interdomain Binding and Reaction Rate," *Biochemistry* 33:2716–2725 (1994).

Richardson and Schepartz, "Tethered Oligonucleotide Probes. A Strategy for the Recognition of Structured RNA," *J. Am. Chem. Soc.* 113:5109–5111 (1991).

Robertson et al., "Purification and Properties of a Specific *Escherichia coli* Ribonuclease which Cleaves a Tyrosine Transfer Ribonucleic Acid Precursor," *J. Biol. Chem.* 247:5243–5251 (1972).

Rosemeyer and Seela, "72. 1(2'–Deoxy–γ–D–xylofuranosyl)thymine Building Blocks for Solid–Phase Synthesis and Properties of Oligo(2–Deoxyxylonucleotides)," *Helvetica Chimica Acta* 74:748–760 (1991).

Russell et al., "Reactions of 2–Acyloxyisobutyrl Halides with Nucleosides. II. Reactions of Adenosine," *J. Am. Chem. Soc.* 95:4025–4030 (1973).

Ryan et al., "Intramolecular Displacement by Neighboring O–Thionobenzoate. Synthesis of 3'–Thioadenosine," *J. Org. Chem.* 33:1783–1789 (1968).

Santagati et al., "Oligonucleotide Squelching Reveals the Mechanism of Estrogen Receptor Autologous Down–Regulation," *Molecular Endocrinology* 11:938–949 (1997).

Santoro and Joyce, "A general purpose RNA–cleaving DNA enzyme," *Proc. Natl. Acad. Sci. USA* 94:4262–4266 (1997).

Santoro et al., "RNA Cleavage by a DNA Enzyme with Extended Chemical Functionality," *J. Am. Chem. Soc.* 122:2433–2439 (2000).

Sarver et al., "Ribozymes as Potential Anti–HIV–1 Therapeutic Agents" *Science* 247:1222–1225 (1990).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using γ–cyanoethyl protected ribonucleoside phosphoramidites," *Nucl. Acids Res.* 18:5433–5441 (1990).

Schmajuk et al., "Antisense Oligonucleotides with Different Backbones," *The Journal of Biological Chemistry* 274:21783–21789 (1999).

Schmidt et al., "Base and sugar requirements for RNA cleavage of essential nucleoside residues in internal loop B of the hairpin ribozyme: implications for secondary structure," *Nucleic Acids Research* 24:573–581 (1996).

Scott et al., "The crystal structure of an All–RNA hammerhead ribozyme: A proposed mechanism for RNA catalytic cleavage," *Cell* 81:991–1002 (1995).

Seela and Kaiser, "Oligodeoxyribonucleotides containing 1,3–propanediol as nucleoside substitute," *Nucleic Acids Research* 15:3113–3129 (1987).

Seela et al., "122. Xylose–DNA Containing the Four Natural Bases," *Helvetica Chimica Acta* 79:1451–1461 (1996).

Seela et al., "83. 1(2'–Deoxy–γ–D–xylofuranosyl)cytosine: Base Pairing of Oligonucleotides with a Configurationally Altered Sugar–Phosphate Backbone," *Helvetica Chimica Acta* 77:883–8986 (1994).

Shabarova et al., "Chemical ligation of DNA: The first non–enzymatic assembly of a biologically active gene," *Nucleic Acids Research* 19:4247–4251 (1991).

Shibahara et al., "Site–directed cleavage of RNA," *Nucleic Acids Research* 15:4403–4415 (1987).

Silverman et al., "Selective RNA Cleavage by Isolated Rnase L. Activated with 2–5A Antisense Chimeric Oligonucleotides," *Methods in Enzymology* 313:522–553 (1999).

Sontheimer et al., "Metal ion catalysis during splicing of premessenger RNA," *Nature* 388:801–805 (1997) (vol. No. mistakenly referred to as 308).

Stein et al., "A Specificity Comparison of Four Antisense types: Morpholino, 2'–O'Methyl RNA, DNA, and Phosphorothioate DNA," Antisense N.A. Drug Dev. 7:151 (1997).

Stein and Cheng, "Antisense Oligonucleotides as Therapeutic Agents—Is the Bullet Really Magical?" *Science* 261:1004–1288 (1993).

Strobel et al., "Exocyclic Amine of the Conserved G–U Pair at the Cleavage Site of the Tetrahymena Ribozyme Contributes to 5'–Splice Site Selection and Transition State Stabilization," *Biochemistry* 35:1201–1211 (1996).

Strobel et al., "Minor Groove Recognition of the Conserved G–U Pair at the Tetrahymena Ribozyme Reaction Site," *Science* 267:675–679 (1995).

Strobel et al., "The 2,6–Diaminopurine Riboside–5–Methylisocytidine Wobble Base Pair: An Isoenergetic Substitution for the Study of G–U Pairs in RNA," *Biochemistry* 33:13824–13835 (1994).

Sullenger and Cech, "Ribozyme–mediated repair of defective mRNA by targeted trans–splicing," *Nature* 371:619–622 (1994).

Sullenger and Cech, "Tethering Ribozymes to a Retroviral Packaging Signal for Destruction of Viral RNA," *Science* 262:1566–1569 (1993).

Sun et al., "Synthesis of 3'–thioribonucleosides and their incorporation into oligoribonucleotides via phosphoramidite chemistry," *RNA* 3:1352–1363 (1997).

Szostak, "In Vitro Genes," *TIBS* 17:89–93 (1993).

Taira et al., "Construction of a novel RNA–transcript–trimming plasmid which can be used both in vitro in place of run–off and (G)–free transcriptions and in vivo as multi–sequences transcription vectors," *Nucleic Acids Research* 19:5125–5130 (1991).

Tang et al., "Examination of the catalytic fitness of the hammerhead ribozyme by in vitro selection," *RNA* 3:914–925 (1997).

Tazawa et al., "L–Adenylyl–(3'–5')–L–adenosine and L–Adenylyl–(2'–5')–L–adenosine," *Biochemistry* 9:3499–3514 (1970).

Thompson et al., "Improved accumulation and activity of ribozymes expressed from a tRNA–based RNA polymerase III promoter," *Nucleic Acids Research* 23:2259–2268 (1995).

Tidd et al., "Evaluation of N–ras anti–sense, sense and nonsense sequence methylphosphonate oligonucleotide analogues," *Anti–Cancer Drug Design* 3:117–127 (1988).

Torrence et al., "Targeting RNA for degradation with a (2'–5') oligoadenylate–antisense chimera," *Proc. Natl. Acad. Sci. USA* 90:1300–1304 (1993).

Turner et al., "Improved Parameters for Prediction of RNA Structure," *Cold Spring Harbor Symposia on Quantitative Biology* vol. LII, pp. 123–133 (1987).

Turner et al., "Free Energy Increments for Hydrogen Bonds in Nucleic Acids Base Pairs," *J. Am. Chem. Soc.* 109:3783–3785 (1987).

Tyler et al., "Specific gene blockade shows that peptide nucleic acids readily enter neuronal cells in vivo," *FEBS Letters* 421:280–284 (1998).

Tyler et al., "Peptide nucleic acids targeted to the neurotensin receptor and administered i.p. cross the blood–brain barrier and specifically reduce gene expression," *Proc. Natl. Acad. Sci. USA* 96:7053–7058 (1999).

Uhlenbeck, "A Small Catalytic Oligoribonucleotide," *Nature* 328:596–600 (1987) (this is listed as Nature 327 in the various specifications, but it is actually 328).

Uhlmann and Peyman, "Antisense Oligonucleotides: A New Therapeutic Principle," *Chemical Reviews* 90:544–584 (1990).

Usman and Cedergren, "Exploiting the chemical synthesis of RNA," *TIBS* 17:334–339 (1992).

Usman et al., WO 95/06731 published Mar. 9, 1995, PCT/US94/09342 filed Aug. 19, 1994 for "Non–Nucleotide Containing Enzymatic Nucleic Acid".

Usman and McSwiggen, "CH. 30—Catalytic RNA (Ribozymes) as Drugs," *Annual Reports in Medicinal Chemistry* 30:285–294 (1995).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Usman et al., "Chemical modification of hammerhead ribozymes: activity and nuclease resistance," *Nucleic Acids Symposium Series* 31:163–164 (1994).

Usman et al., "Hammerhead ribozyme engineering," *Current Opinion in Structural Biology* 1:527–533 (1996).

Vaish et al., "Isolation of Hammerhead Ribozymes with Altered Core Sequences by in Vitro Selection," *Biochemistry* 36:6495–6501 (1997).

Ventura et al., "Activation of HIV–Specific Ribozyme Activity by Self–Cleavage," *Nucleic Acids Research* 21:3249–3255 (1993).

Verma and Eckstein, "Modified Oligonucleotides: Synthesis and Strategy for Users," *Annu. Rev. Biochem.* 67:99–134 (1998).

Vyle et al., "Sequence– and Strand–Specific Cleavage in Oligodeoxyribonucleotides and DNA Containing 3'–Thiothymidine," *Biochemistry* 31:3012–3018 (1992).

Warashina, et al., Extremely High and Specific Activity of DNA Enzymes in Cells with a Philadelphia Chromosome, *Chemistry & Biology*, 6(4):237–250 (1999).

Weerasinghe et al., "Resistance to Human Immunodeficiency Virus Type 1 (HIV–1) Infection in Human CD4+ Lymphocyte–Derived Cell Lines Conferred by Using Retroviral Vectors Expressing an HIV–1 RNA–Specific Ribozyme," *Journal of Virology* 65:5531–5534 (1994).

Weinstein et al., "Synthesis and Characterization of an RNA Dinucleotide Containing a 3'–S–Phosphorothiolate Linkage," *J. Am. Chem. Soc.* 118:10341–10350 (1996).

Werner and Uhlenbeck, "The effect of base mismatches in the substrate recognition helices of hammerhead ribozymes on binding and catalysis," *Nucleic Acids Research* 23:2092–2096 (1995).

Williard et al., "Paradoxical production of target protein using antisense RNA expression vectors," *Gene* 149:21–24 (1994).

Wincott et al., "Synthesis, deprotection, analysis and purification of RNA and ribozymes," *Nucleic Acids Research* 23(14):2677–2684 (1995).

Wincott et al., "A Practical Method for the Production of RNA and Ribozymes," *Methods in Molecular Biology* 74:59–69 (1997).

Wu–Pong, "Oligonucleotides: Opportunities for Drug Therapy and Research," *Biopharm.* Nov. 1994.

Yu et al., "A Hairpin Ribozyme Inhibits Expression of Diverse Strains of Human Immunodeficiency Virus Type 1," *Proc. Nat. Acad. Sci. USA* 90:6340–6344 (1993).

Yuan et al., "Targeted cleavage of mRNA by human RNase P," *Proc. Natl. Acad. Sci. USA* 89:8006–8010 (1992).

Zarrinkar and Williamson, "The P9.1–P9.2 peripheral extension helps guide folding of the Tetrahymena ribozyme," *Nucleic Acids Research* 24:854–858 (1996).

Zaug et al., "The Tetrahymena Ribozyme Acts Like an RNA Restriction Endonuclease," *Nature* 324:429–433 (1986).

Zhou et al., "Synthesis of Functional mRNA in Mammalian Cells by Bacteriophage T3 RNA Polymerase," *Mol. Cell. Biol.* 10:4529–4537 (1990).

Zimmerly et al., "A Group II Intron RNA is a Catalytic Component of a DNA Endonuclease Involved in Intron Mobility," *Cell* 83:529–538 (1995).

* cited by examiner

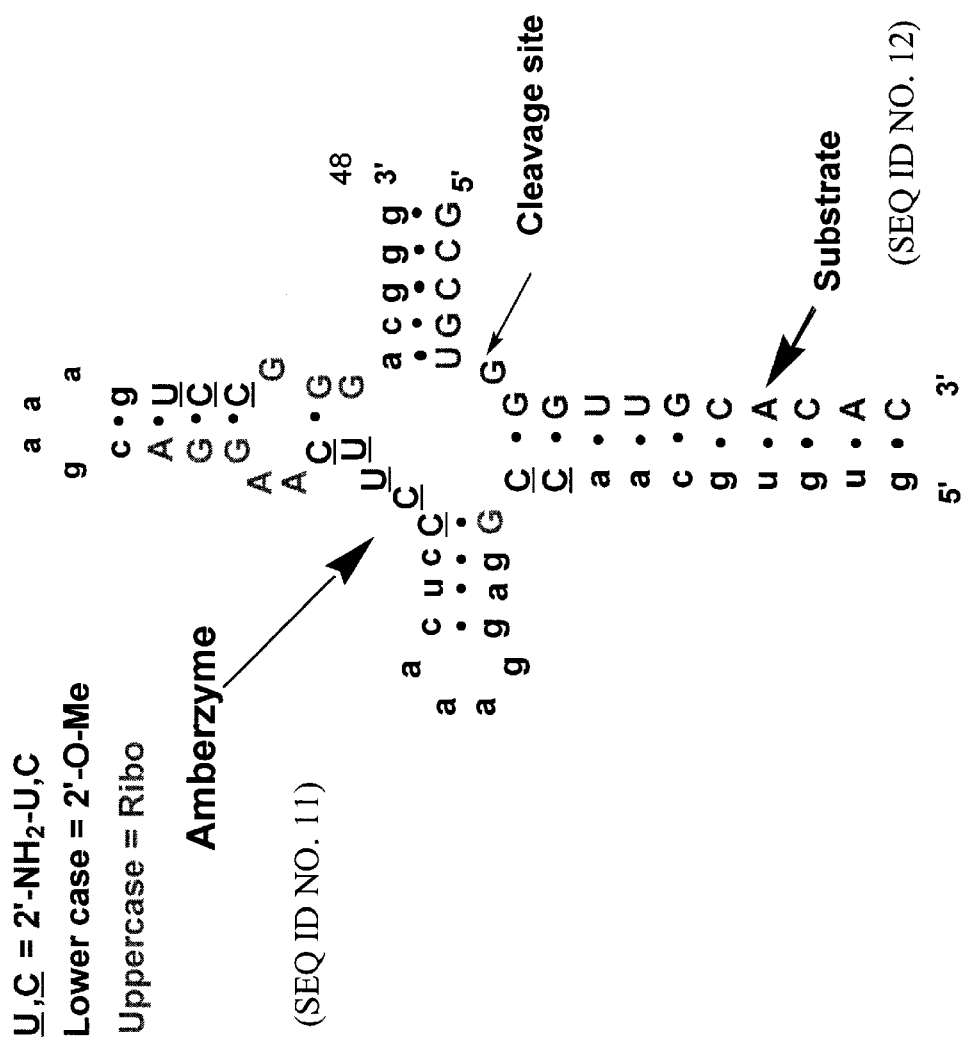

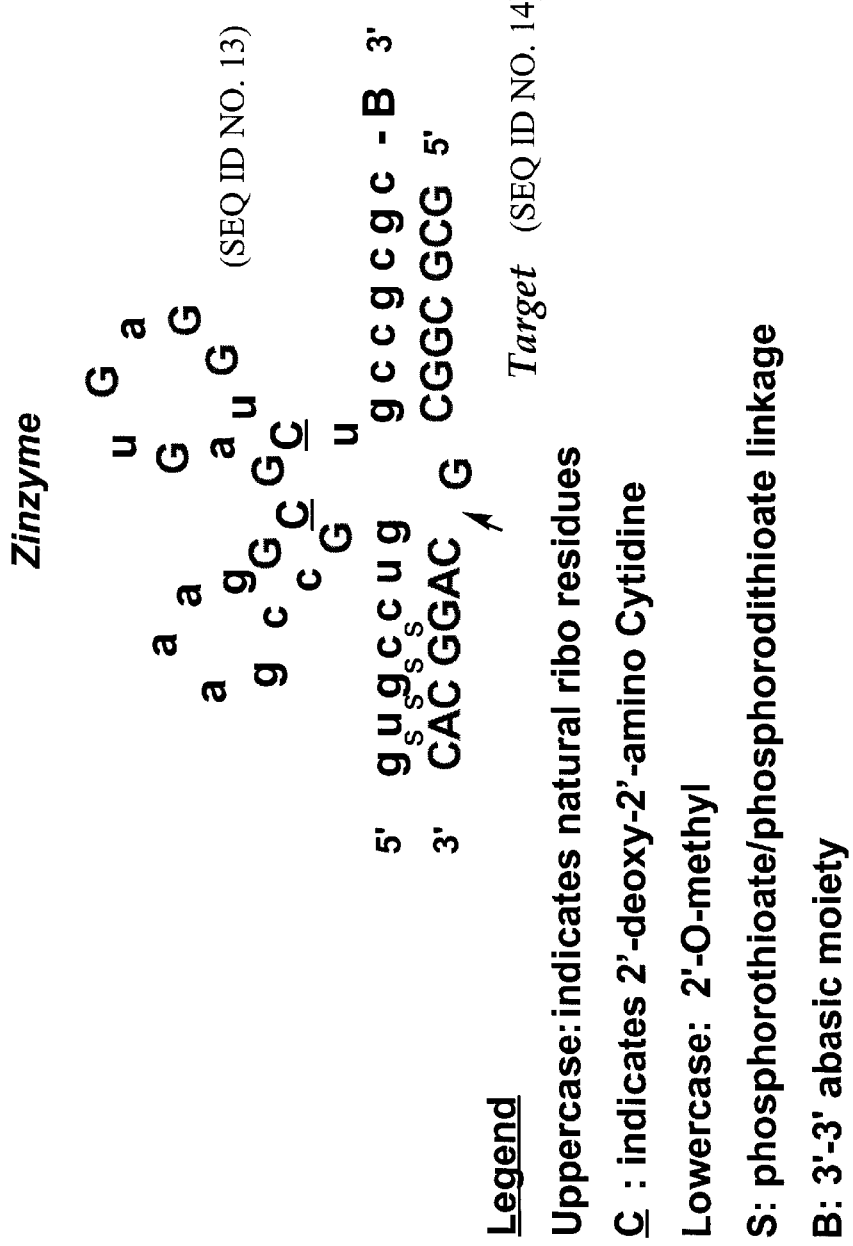
*Figure 3: Stabilized Zinzyme Ribozyme Motif*

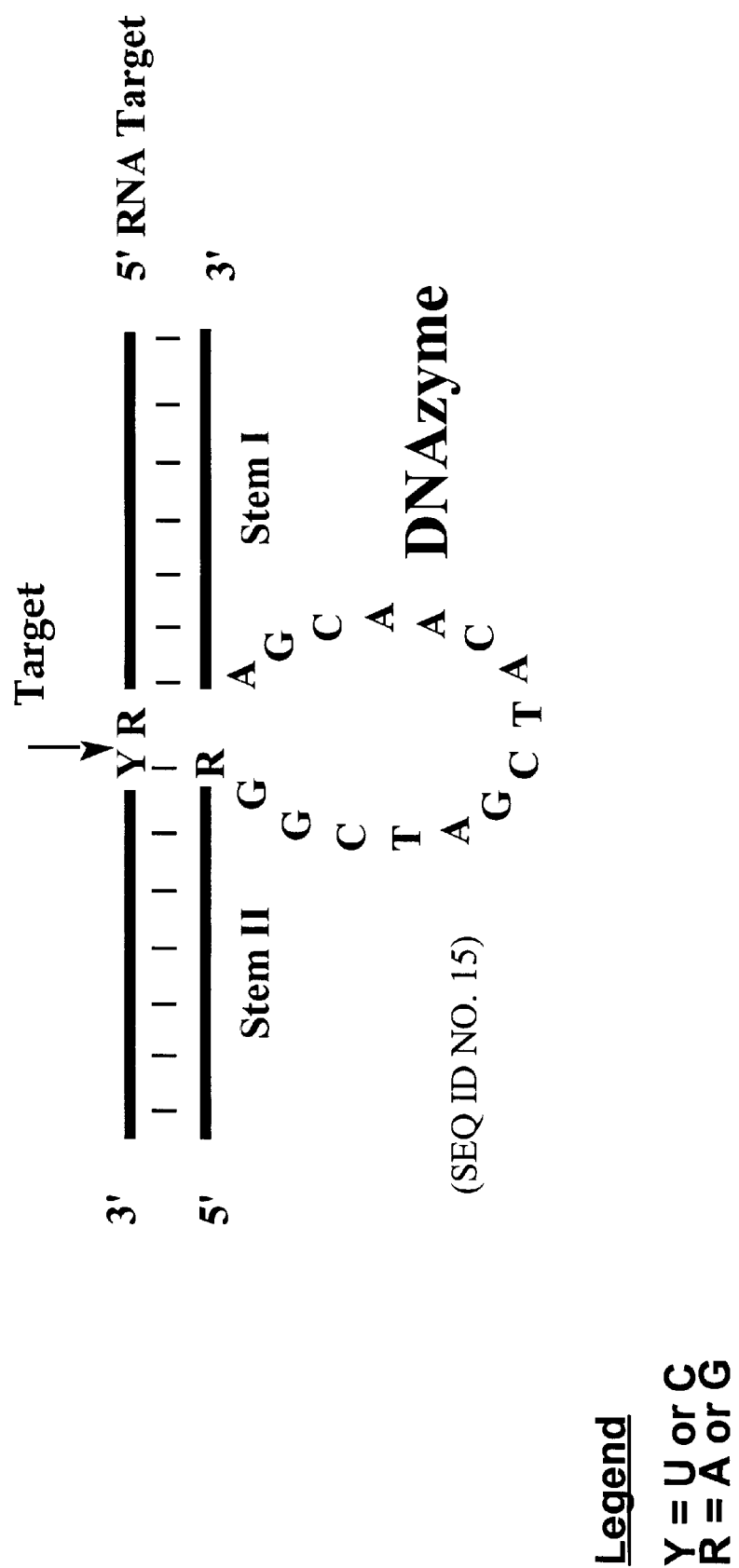
Figure 4: DNAzyme Motif

SEQUENCE LISTING

<160> NUMBER OF SEQ ID NOS: 15

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Active
      GeneBloc Sequence
<221> NAME/KEY: misc_feature
<222> LOCATION: (1)..(7)
<223> OTHER INFORMATION: 2'-O-Methyl
<221> NAME/KEY: misc_feature
<222> LOCATION: (17)..(22)
<223> OTHER INFORMATION: 2'-O-Methyl
<221> NAME/KEY: misc_feature
<222> LOCATION: (1)..(3)
<223> OTHER INFORMATION: Phosphorothioate 3'-Internucleotide Linkage
<221> NAME/KEY: misc_feature
<222> LOCATION: (8)..(16)
<223> OTHER INFORMATION: Phosphorothioate 3'-Internucleotide Linkage
<221> NAME/KEY: misc_feature
<222> LOCATION: (20)..(22)
<223> OTHER INFORMATION: Phosphorothioate 3'-Internucleotide Linkage

<400> SEQUENCE: 1
ugauucuttc caggctcaug aat                                          23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Mismatch
      control GeneBloc sequence
<221> NAME/KEY: misc_feature
<222> LOCATION: (1)..(7)
<223> OTHER INFORMATION: 2'-O-Methyl
<221> NAME/KEY: misc_feature
<222> LOCATION: (17)..(22)
<223> OTHER INFORMATION: 2'-O-Methyl
<221> NAME/KEY: misc_feature
<222> LOCATION: (1)..(3)
<223> OTHER INFORMATION: Phosphorothioate 3'-Internucleotide Linkage
<221> NAME/KEY: misc_feature
<222> LOCATION: (8)..(16)
<223> OTHER INFORMATION: Phosphorothioate 3'-Internucleotide Linkage
<221> NAME/KEY: misc_feature
<222> LOCATION: (20)..(22)
<223> OTHER INFORMATION: Phosphorothioate 3'-Internucleotide Linkage

<400> SEQUENCE: 2
ugauucuttg cccgatcaug aat                                          23

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Active
      GeneBloc Sequence
<221> NAME/KEY: misc_feature
<222> LOCATION: (1)..(1)
<223> OTHER INFORMATION: 3'-3' inverted abasic moiety
<221> NAME/KEY: misc_feature
<222> LOCATION: (25)..(25)
<223> OTHER INFORMATION: 3'-3' inverted abasic moiety
<221> NAME/KEY: misc_feature
<222> LOCATION: (2)..(8)
<223> OTHER INFORMATION: 2'-O-Methyl
<221> NAME/KEY: misc_feature
<222> LOCATION: (18)..(24)

```
<223> OTHER INFORMATION: 2'-O-Methyl
<221> NAME/KEY: misc_feature
<222> LOCATION: (9)..(17)
<223> OTHER INFORMATION: Phosphorothioate 3'-Internucleotide Linkage

<400> SEQUENCE: 3
nugauucutt ccaggctcau gaaun                                              25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Mismatch
      control GeneBloc sequence
<221> NAME/KEY: misc_feature
<222> LOCATION: (1)..(1)
<223> OTHER INFORMATION: 3'-3' inverted abasic moiety
<221> NAME/KEY: misc_feature
<222> LOCATION: (25)..(25)
<223> OTHER INFORMATION: 3'-3' inverted abasic moiety
<221> NAME/KEY: misc_feature
<222> LOCATION: (2)..(8)
<223> OTHER INFORMATION: 2'-O-Methyl
<221> NAME/KEY: misc_feature
<222> LOCATION: (18)..(24)
<223> OTHER INFORMATION: 2'-O-Methyl
<221> NAME/KEY: misc_feature
<222> LOCATION: (9)..(17)
<223> OTHER INFORMATION: Phosphorothioate 3'-Internucleotide Linkage

<400> SEQUENCE: 4
nugauucutt gcccgatcau gaaun                                              25

<210> SEQ ID NO 5
<211> LENGTH: 15
<212> TYPE: RNA
<213> ORGANISM: Artificial Sequence
<220> FEATURE:
<223> OTHER INFORMATION: Description of Artificial Sequence: Generic
      Target Sequence
<221> NAME/KEY: misc_feature
<222> LOCATION: (1)..(6)
<223> OTHER INFORMATION: n stands for a, c, g, or u
<221> NAME/KEY: misc_feature
<222> LOCATION: (9)..(15)
<223> OTHER INFORMATION: n stands for a, c, g, or u

<400> SEQUENCE: 5
nnnnnnuhnn nnnnn                                                         15

<210> SEQ ID NO 6
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(7)
<223> OTHER INFORMATION: n stands for a, c, g, or u
<221> NAME/KEY: misc_feature
<222> LOCATION: (16)..(18)
<223> OTHER INFORMATION: n stands for a, c, g, or u
<221> NAME/KEY: misc_feature
<222> LOCATION: (23)..(25)
<223> OTHER INFORMATION: n stands for a, c, g, or u
<221> NAME/KEY: misc_feature
<222> LOCATION: (31)..(36)
<223> OTHER INFORMATION: n stands for a, c, g, or u
<221> NAME/KEY: misc_feature
<222> LOCATION: (1)..(8)
<223> OTHER INFORMATION: 2'-O-Methyl
```

```
<221> NAME/KEY: misc_feature
<222> LOCATION: (12)..(12)
<223> OTHER INFORMATION: 2'-O-Methyl
<221> NAME/KEY: misc_feature
<222> LOCATION: (14)..(26)
<223> OTHER INFORMATION: 2'-O-Methyl
<221> NAME/KEY: misc_feature
<222> LOCATION: (28)..(29)
<223> OTHER INFORMATION: 2'-O-Methyl
<221> NAME/KEY: misc_feature
<222> LOCATION: (31)..(36)
<223> OTHER INFORMATION: 2'-O-Methyl
<221> NAME/KEY: misc_feature
<222> LOCATION: (9)..(9)
<223> OTHER INFORMATION: 2'-deoxy-2'-C-Allyl

<400> SEQUENCE: 6
nnnnnnncug augagnnnga aannncgaaa nnnnnn                                  36

<210> SEQ ID NO 7
<211> LENGTH: 14
<212> TYPE: RNA
<213> ORGANISM: Artificial Sequence
<220> FEATURE:
<223> OTHER INFORMATION: Description of Artificial Sequence: Generic
      Target Sequence
<221> NAME/KEY: misc_feature
<222> LOCATION: (1)..(5)
<223> OTHER INFORMATION: n stands for a, c, g, or u
<221> NAME/KEY: misc_feature
<222> LOCATION: (8)..(14)
<223> OTHER INFORMATION: n stands for a, c, g, or u

<400> SEQUENCE: 7
nnnnnchnnn nnnn                                                          14

<210> SEQ ID NO 8
<211> LENGTH: 35
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(7)
<223> OTHER INFORMATION: n stands for a, c, g, or u
<221> NAME/KEY: misc_feature
<222> LOCATION: (16)..(18)
<223> OTHER INFORMATION: n stands for a, c, g, or u
<221> NAME/KEY: misc_feature
<222> LOCATION: (23)..(25)
<223> OTHER INFORMATION: n stands for a, c, g, or u
<221> NAME/KEY: misc_feature
<222> LOCATION: (31)..(35)
<223> OTHER INFORMATION: n stands for a, c, g, or u
<221> NAME/KEY: misc_feature
<222> LOCATION: (1)..(8)
<223> OTHER INFORMATION: 2'-O-Methyl
<221> NAME/KEY: misc_feature
<222> LOCATION: (12)..(12)
<223> OTHER INFORMATION: 2'-O-Methyl
<221> NAME/KEY: misc_feature
<222> LOCATION: (14)..(26)
<223> OTHER INFORMATION: 2'-O-Methyl
<221> NAME/KEY: misc_feature
<222> LOCATION: (28)..(29)
<223> OTHER INFORMATION: 2'-O-Methyl
<221> NAME/KEY: misc_feature
<222> LOCATION: (31)..(35)
<223> OTHER INFORMATION: 2'-O-Methyl
<221> NAME/KEY: misc_feature
<222> LOCATION: (30)..(30)
<223> OTHER INFORMATION: n stands for Inosine
<221> NAME/KEY: misc_feature
<222> LOCATION: (9)..(9)
```

<223> OTHER INFORMATION: 2'-deoxy-2'-C-Allyl

<400> SEQUENCE: 8
nnnnnnncug augagnnnga aannncgaan nnnnn    35

<210> SEQ ID NO 9
<211> LENGTH: 15
<212> TYPE: RNA
<213> ORGANISM: Artificial Sequence
<220> FEATURE:
<223> OTHER INFORMATION: Description of Artificial Sequence: Generic Target Sequence
<221> NAME/KEY: misc_feature
<222> LOCATION: (1)..(6)
<223> OTHER INFORMATION: n stands for a, c, g, or u
<221> NAME/KEY: misc_feature
<222> LOCATION: (9)..(15)
<223> OTHER INFORMATION: n stands for a, c, g, or u

<400> SEQUENCE: 9
nnnnnnygnn nnnnn    15

<210> SEQ ID NO 10
<211> LENGTH: 35
<212> TYPE: RNA
<213> ORGANISM: Artificial Sequence
<220> FEATURE:
<223> OTHER INFORMATION: Description of Artificial Sequence: Enzymatic Nucleic Acid
<221> NAME/KEY: misc_feature
<222> LOCATION: (1)..(7)
<223> OTHER INFORMATION: n stands for a, c, g, or u
<221> NAME/KEY: misc_feature
<222> LOCATION: (29)..(35)
<223> OTHER INFORMATION: n stands for a, c, g, or u
<221> NAME/KEY: misc_feature
<222> LOCATION: (1)..(8)
<223> OTHER INFORMATION: 2'-O-Methyl
<221> NAME/KEY: misc_feature
<222> LOCATION: (13)..(16)
<223> OTHER INFORMATION: 2'-O-Methyl
<221> NAME/KEY: misc_feature
<222> LOCATION: (18)..(35)
<223> OTHER INFORMATION: 2'-O-Methyl
<221> NAME/KEY: misc_feature
<222> LOCATION: (11)..(11)
<223> OTHER INFORMATION: Phosphorothioate 3'-Internucleotide Linkage

<400> SEQUENCE: 10
nnnnnnnuga uggcaugcac uaugcgcgnn nnnnn    35

<210> SEQ ID NO 11
<211> LENGTH: 48
<212> TYPE: RNA
<213> ORGANISM: Artificial Sequence
<220> FEATURE:
<223> OTHER INFORMATION: Description of Artificial Sequence: Enzymatic Nucleic Acid
<221> NAME/KEY: misc_feature
<222> LOCATION: (1)..(8)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (32)..(37)
<223> OTHER INFORMATION: 2'-O-Methyl
<221> NAME/KEY: misc_feature
<222> LOCATION: (44)..(48)
<223> OTHER INFORMATION: 2'-O-Methyl
<221> NAME/KEY: misc_feature
<222> LOCATION: (9)..(10)
<223> OTHER INFORMATION: 2'-deoxy-2'-amino
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (38)..(40)
<223> OTHER INFORMATION: 2'-deoxy-2'-amino

<400> SEQUENCE: 11
gugugcaacc ggaggaaacu cccuucaagg acgaaagucc gggacggg                48

<210> SEQ ID NO 12
<211> LENGTH: 16
<212> TYPE: RNA
<213> ORGANISM: Artificial Sequence
<220> FEATURE:
<223> OTHER INFORMATION: Description of Artificial Sequence: Target
      Nucleic Acid Sequence

<400> SEQUENCE: 12
gccguggguu gcacac                                                   16

<210> SEQ ID NO 13
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(7)
<223> OTHER INFORMATION: 2'-O-Methyl
<221> NAME/KEY: misc_feature
<222> LOCATION: (36)..(36)
<223> OTHER INFORMATION: 3'-3' inverted abasic moiety
<221> NAME/KEY: misc_feature
<222> LOCATION: (9)..(15)
<223> OTHER INFORMATION: 2'-O-Methyl
<221> NAME/KEY: misc_feature
<222> LOCATION: (19)..(19)
<223> OTHER INFORMATION: 2'-O-Methyl
<221> NAME/KEY: misc_feature
<222> LOCATION: (21)..(21)
<223> OTHER INFORMATION: 2'-O-Methyl
<221> NAME/KEY: misc_feature
<222> LOCATION: (23)..(23)
<223> OTHER INFORMATION: 2'-O-Methyl
<221> NAME/KEY: misc_feature
<222> LOCATION: (26)..(26)
<223> OTHER INFORMATION: 2'-O-Methyl
<221> NAME/KEY: misc_feature
<222> LOCATION: (28)..(35)
<223> OTHER INFORMATION: 2'-O-Methyl
<221> NAME/KEY: misc_feature
<222> LOCATION: (1)..(4)
<223> OTHER INFORMATION: Phosphorothioate 3'-Internucleotide Linkage
<221> NAME/KEY: misc_feature
<222> LOCATION: (17)..(17)
<223> OTHER INFORMATION: 2'-Deoxy-2'-Amino
<221> NAME/KEY: misc_feature
<222> LOCATION: (27)..(27)
<223> OTHER INFORMATION: 2'-Deoxy-2'-Amino

<400> SEQUENCE: 13
gugccuggcc gaaaggcgag ugaggucugc cgcgcn                             36

<210> SEQ ID NO 14
<211> LENGTH: 15
<212> TYPE: RNA
<213> ORGANISM: Artificial Sequence
<220> FEATURE:
<223> OTHER INFORMATION: Description of Artificial Sequence: Target
      Nucleic Acid Sequence

```
<400> SEQUENCE: 14
gcgcggcgca ggcac                                                        15

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence:  DNAzyme
      Motif

<400> SEQUENCE: 15
rggctagcta caacga                                                       16
```

NUCLEIC ACID MOLECULES WITH NOVEL CHEMICAL COMPOSITIONS CAPABLE OF MODULATING GENE EXPRESSION

This patent application in a continuation-in-part of Thompson et al., U.S. Ser. No. 09/103,636, filed Jun. 23, 1998, entitled "NUCLEIC ACID MOLECULES WITH NOVEL CHEMICAL COMPOSITIONS CAPABLE OF MODULATING GENE EXPRESSION", which claims priority from Thompson et al., U.S. Ser. No. 60/082,404, filed Apr. 20, 1998, entitled "NUCLEIC ACID MOLECULES WITH NOVEL CHEMICAL COMPOSITIONS CAPABLE OF MODULATING GENE EXPRESSION". These patent applications are hereby incorporated by reference herein in their entirety including the drawings.

BACKGROUND OF THE INVENTION

This invention relates to novel chemically modified nucleic acid molecules that are capable of modulating gene expression through a variety of mechanisms. Specifically, the invention concerns novel combinations of chemical modifications in an oligonucleotide which enhance nuclease resistance, binding affinity, and/or potency.

The following is a discussion of relevant art, none of which is admitted to be prior art to the present invention.

Since the discovery of the mechanisms underlying gene expression, specifically nucleic acid based transcription and translation, a great deal of effort has been placed on blocking or altering these processes for a variety of purposes, such as understanding biology, gene function, disease processes, and identifying novel therapeutic targets. Approaches involving nucleic acid molecules for modulating gene expression have gained popularity in recent years. For example, nucleic acid molecules have been designed which are capable of binding to specific mRNA sequences by Watson-Crick base pairing interaction and blocking translation (Crooke, 1996, Medicinal Res. Rev. 16, 319–344). Another approach involves complexation of DNA with triplex forming oligonucleotides to prevent transcription of bound DNA sequences thereby inhibiting gene expression (Kim et al., 1998, Biochemistry. 37, 2299–2304). The interaction of antisense oligonucleotides, 2–5A antisense chimera, or ribozymes with target RNA have been used to prevent gene expression. All of these nucleic acid molecules are highly specific to their matching target sequences and therefore can offer lower toxicity compared to traditional approaches such as chemotherapy.

The use of oligonucleotides for modulation of gene expression generally requires stabilization of oligonucleotides from degradation by nucleases that are present in biological systems. Cellular efficacy can be effected if the nucleic acid molecule is degraded before it reaches its desired target. Chemical modifications of nucleic acid molecules have been found to be advantageous in making them inaccessible to degradation by cellular nucleases. Uhlmann and Peyman, 1990, Chem. Reviews 90, 543, review the use of nucleoside modifications to stabilize antisense oligonucleotides. Besides improved stability, chemical modifications have also been shown to increase binding affinity, improve cellular penetration, and enhanced target specificity (Monia et al., 1993, J. Biol. Chem. 268, 14514–14522; Wu-Pong, 1994, BioPharm, 22–33).

One of the most studied and utilized chemical alteration in oligonucleotides has been backbone modifications such as phosphorothioates. Phosphorothioate oligonucleotides are nucleic acid molecules whose phosphodiester linkage has been modified by substituting a sulfur atom in place of an oxygen atom. In addition to increased nuclease resistance, phosphorothioate oligonucleotides are substrates for ribonuclease H (RNase H) (Monia, supra; Crooke et al., 1995, Biochem. J. 3112, 599–608). RNase H is an endonuclease which catalyzes the degradation of RNA in an RNA-DNA heteroduplex (Hostomsky et al., 1993 in Nucleases, Linn et al., eds., Cold Spring Harbor Laboratory Press, NY, 341–376). RNA/DNA heteroduplexes, called Okazaki fragments, are formed naturally during DNA replication. Therefore, the normal function of RNase H is to degrade the RNA portion of the heteroduplex to complete DNA replication. In experiments with $E.$ $coli$ RNase H, the phosphorothioate oligonucleotide activated the enzyme more efficiently (2–5 fold) compared to a standard phosphodiester containing oligonucleotide (Crooke, 1995, supra).

Binding of DNA to RNA is not as thermodynamically favorable as an RNA to RNA interaction (Altmann et al., 1996, Chimia 50, 168–176). Inoe & Ohtsuka, 1987, Nucleic Acids Research 115, 6131, first proposed an oligonucleotide with a central region consisting of oligodeoxynucleotides flanked by 2'-O-methyl modified nucleotide regions. The region of oligodeoxynucleotides in such a chimeric molecule is recognized by RNase H when bound to target RNA; and facilitates cleavage of target RNA by RNase H. (Inoe & Ohtsuka, 1987, FEBS Lett. 215, 327; Shibahara & Morisava, 1987, Nucleic Acids Res. 15, 4403). Such chimeric oligonucleotides were proposed to interact with target RNA more stably than an all DNA oligonucleotide.

Subsequent developments included the introduction of nuclease resistant modifications of the chimeric oligonucleotides, such as methylphosphonates (Tidd & Gibson, 1988, Anticancer Drug Design 3, 117), phosphorothioates (Agrawal & Pederson, 1990, Proc Nat. Acad. Sci. USA 87, 1407), and phosphoramidates (Potts & Runyun, 1991, Proc Nat. Acad. Sci. USA 88, 1516). Additionally, the flanking sequences have been modified with 2'-O-methyl and 2'-F-modifications (Cook, 1993, Antisense Research and Applications, CRC Press, 150–181).

Agrawal et al., U.S. Pat. No. 5,652,355, describe a phosphorothioate-containing nucleic acid molecule with at least two 2'-O-methyl modifications on the 5' and 3' ends.

Agrawal, U.S. Pat. No. 5,652,356, describes an oligonucleotide which consists of a region of 2'-O-substituted oligonucleotide located between two oligodeoxyribonucleotide regions. The DNA regions of this nucleic acid molecule consists of phosphorothioate modifications at every position.

Cook et al., U.S. Pat. No. 5,623,065, describe the use of a nucleic acid molecule which contains an RNase H cleavable region flanked by certain specifically modified nucleotides, for inhibition of gene expression of a ras gene.

Cook et al., U.S. Pat. No. 5,587,362, describe a nucleic acid molecule having "substantially chirally pure inter-sugar linkages", for modulation of gene expression.

Ohtsuka et al., U.S. Pat. No. 5,013,830, describe mixed oligomers having a DNA region and a 2'-O-methyl modified region, useful for modulation of gene expression.

Walder et al., U.S. Pat. No. 5,491,133, describe a method for modulating gene expression using chimeric oligonucleotides with 3'-phosphodiester linkage modifications.

Cohen et al., U.S. Pat. No. 5,276,019, and Cohen et al., U.S. Pat. No. 5,264,423 describe the use of oligodeoxynucleotides of no more than 32 nucleotides in length, containing at least one phosphorothioate internucleoside linkage which are capable of preventing foreign nucleic acid replication.

Cohen et al., U.S. Pat. No. 5,286,717, describe an oligodeoxyribonucleotide with at least one phosphorothioate modification capable of inhibiting oncogenes.

Sproat et al., U.S. Pat. No. 5,334,711, describe 2'-O-R modified hammerhead and hairpin ribozymes, where R is alkyl, alkynyl or alkenyl.

Crooke et al., 1996, Exp. Opin. Ther. Patents 6, 855, list and discuss various patents and PCT publications in the field of antisense technology.

Sproat et al., U.S. Pat. No. 5,678,731, describe 2'-O-R modified oligonucleotides where R is alkyl, alkynyl or alkenyl.

Usman et al., U.S. Pat. No. 5,652,094, describe enzymatic nucleic acid molecules which include nucleic acid analogues or deoxyribonucleotides.

Joyce, International Publication No. WO 96/17086, describes a DNA enzyme capable of cleaving RNA.

Rossi et al., U.S. Pat. No. 5,144,019, describe chimeric hammerhead ribozymes with the binding arms and stem II region modified with deoxyribonucleotides.

Arrow et al., U.S. Pat. Nos. 5,989,912 and 5,849,902, describe three component chimeric antisense oligonucleotides.

Tullis, U.S. Pat. No. 5,919,619, describes methods for inhibiting target protein expression with specific antisense nucleic acid molecules.

Walder et al., U.S. Pat. No. 5,144,019, describe the use of specific oligodeoxynucleotides modified at the 3'-terminal internucleotide link as therapeutic agents by a method of hybridizing the modified oligonucleotide to a complementary sequence within a targeted mRNA and cleaving the mRNA within the RNA-DNA helix by the enzyme RNaseH to block the expression of the corresponding gene.

Crooke et al., U.S. Pat. No. 6,001,653, describe the use of specific antisense oligonucleotides that that bind to a target RNA molecule and cleave the RNA via RNAse H mediated activity.

Molecules have also been devised which include nonnucleotides capable of binding to nucleic acid. These peptide nucleic acid (PNA) molecules bind by Watson-Crick base-pairing and can also function through an antisense mechanism. These molecules have been used to augment hammerhead ribozyme activity by altering the structure of target RNAs and increasing accessibility of cleavage sites (Jankowsky et al., 1997, Nucleic Acids Research 25, 2690–2693).

SUMMARY OF THE INVENTION

This invention relates to novel nucleic acid molecules which are useful for modulation of gene expression. The nucleic acid molecule of the instant invention are distinct from other nucleic acid molecules known in the art. Specifically, the nucleic acid molecules of the present invention have novel combinations of chemical modifications and are capable of binding to RNA or DNA to facilitate modulation of gene expression. These novel combinations of chemical modifications can be used to form antisense oligonucleotides, triplex forming oligonucleotides, 2–5A antisense chimera, and enzymatic nucleic acid molecules.

In one embodiment, the invention features a nucleic acid molecule having the following formulae: Formula I:

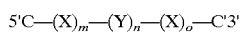

Formula II:

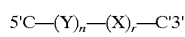

Formula III:

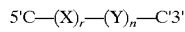

In a another embodiment, the invention features an enzymatic nucleic acid molecule having the formula:
Formula IV:

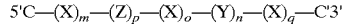

Formula V:

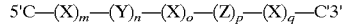

Formula VI:

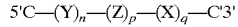

Formula VII

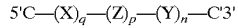

In each of the above formula (I–VII), X represents independently a nucleotide which can be same or different; where m and o are integers independently greater than or equal to 4 and preferably less than about 100, more specifically 5, 6, 7, 8, 9, 10, 11, 12, 15, or 20; r is an integer greater than or equal to four, more specifically 5, 6, 7, 10, 15, or 20; the nucleic acid molecule can be symmetric (m equal to O) or asymmetric (m not equal to O); $(X)_m$, $(X)_o$, and $(X)_q$ are oligonucleotides which are of sufficient length to stably interact independently with a target nucleic acid molecule (the target can be an RNA, DNA or RNA/DNA mixed polymers); Y represents independently a deoxyribonucleotide which can be same or different; n is an integer greater than or equal to 4, specifically 5, 6 7, 8, 9, 10, 11, or 12; Z represents an oligonucleotide including nucleotides capable of facilitating the cleavage of a target sequence; p is of length greater than or equal to 4 but less than 100, preferably 5, between 10–20, specifically 25–55, specifically between 30–45, more specifically 35–50; q is an integer greater than or equal to 0, preferably 1, 2, 3, 4, 5, 6, 7, 8, 10, 15, 20; _represents a chemical linkage (e.g. a phosphate ester linkage, amide linkage or others known in the art); and each $(X)_m$, $(X)_o$, $(X)_r$, $(X)_q$, and/or $(Y)_n$ independently comprise phosphorothioate linkages, more specifically each $(X)_m$, $(X)_o$, $(X)_r$, $(X)_q$, and/or $(Y)_n$ independently comprise at least one phosphodiester linkage and/or one phosphorothioate linkage or a mixture thereof; each C and C' independently represents a cap structure which can independently be present or absent; and $(Z)_p$ can optionally include a phosphorothioate linkage. The nucleotides in the each of the formula I–VII are unmodified or modified at the sugar, base, and/or phosphate as known in the art.

In another embodiment, each of X represents independently a nucleotide which can be same or different; where m and o are integers independently greater than or equal to 5; $(X)_m$ and $(X)_o$ are oligonucleotides which are of sufficient length to stably interact independently with a target nucleic acid molecule; each $(X)_r$ comprises independently at least one phosphodiester linkage and/or one phosphorothioate linkage; Y represents independently a deoxyribonucleotide which can be same or different; $(Y)_n$ is an oligonucleotide which is of sufficient length to stably interact independently with a target nucleic acid molecule; n is an integer greater than or equal to 4; each $(X)_m$, and $(X)_o$ comprise independently at least one phosphodiester linkage and/or one phosphorothioate linkage or a mixture thereof; $(Y)_n$ comprises a phosphorothioate linkage or a phosphorodithioate linkage or a 5'-S-phosphorothioate, or 5'-S-phosphorodithioate, or a 3'—S— phosphorothioate or a 3'-S-phosphorodithioate linkage or a mixture thereof; and each C and C' independently represents a cap structure which can independently be present or absent.

In one embodiment, Z in the above formulae IV–VII comprises a hammerhead, inozyme, G-cleaver, zinzyme, DNAzyme, or amberzyme enzymatic nucleic acid molecule.

In another embodiment, the invention features a nucleic acid molecule having the following formulae:

XI:

XII:

XIII:

XIV:

In each of the above Formulae (XI–XIV), r stands for any 2'-O-alkyl nucleotide, for example 2'-O-methyl adenosine, 2'-O-methyl guanosine, 2'-O-methyl cytidine, or 2'-O-methyl uridine; D stands for any deoxynucleotide or 2'-arabinofluoro nucleotide, s stands for a phosphorothioate, phosphorodithio ate, 5'-thiophosphate, 3'-thiophosphate or methylphosphonate internucleotide linkage; p stands for a phosphodiester internucleotide linkage; x stands for a 2'-O-alkyl-thio-alkyl nucleotide, for example 2'-methyl-thio-methyl adenosine, 2'-methyl-thio-methyl guanosine, 2'-methyl-thio-methyl cytidine, or 2'-methyl-thio-methyl uridine; and iB stands for an inverted abasic moiety, for example a 3',3' or 5',5'-linked deoxyabasic moiety. The linkage between the 3',3' or 5',5'-linked deoxyabasic moiety can be a phosphorothioate, phosphorodithioate, 5'-thiophosphate, 3'-thiophosphate, methylphosphonate, or phosphodiester internucleotide linkage.

In one embodiment, a nucleic acid molecule of the invention is an antisense nucleic acid molecule.

In another embodiment, a nucleic acid molecule of the invention further comprises a 2–5A antisense chimera.

The present invention also features a method of modulating the expression of a gene in a cell, for example a mammalian cell or human cell, comprising the step of administering to the cell a nucleic acid molecule of the invention under conditions suitable for the down regulation of said gene.

In one embodiment, the invention features a pharmaceutical composition comprising a nucleic acid molecule of the invention in a pharmaceutically acceptable carrier.

In another embodiment, the invention features a method of administering to a cell a nucleic acid molecule of the invention, comprising contacting the cell, for example a mammalian cell or human cell, with the nucleic acid molecule under conditions suitable for the administration. The administration can be in the presence of a delivery reagent, for example, a lipid, cationic lipid, or liposome.

The term "nucleotide" as used herein, refers to a heterocyclic nitrogenous base in N-glycosidic linkage with a phosphorylated sugar. Nucleotides are recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; Uhlman & Peyman, supra all are hereby incorporated by reference herein). There are several examples of modified nucleic acid bases known in the art as summarized by Limbach et al., 1994, Nucleic Acids Res. 22, 2183. Some of the non-limiting examples of chemically modified and other natural nucleic acid bases that can be introduced into nucleic acids include, for example, inosine, purine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid, 2-thiocytidine, threonine derivatives and others (Burgin et al., 1996, Biochemistry, 35, 14090; Uhlman & Peyman, supra). By "modified bases" in this aspect is meant nucleotide bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

The term "2'-arabinofluoro nucleotide" as used herein, refers to a nucleotide comprising a 2'-fluoro group in an arabinofuranosyl configuration.

The term "unmodified nucleotide" as used herein, refers to a nucleotide with one of the bases adenine, cytosine, guanine, thymine, uracil joined to the 1' carbon of β-D-ribofuranose.

The term "modified nucleotide" as used herein, refers to a nucleotide which contains a modification in the chemical structure of an unmodified nucleotide base, sugar and/or phosphate.

The term "sufficient length" as used herein, refers to an oligonucleotide of greater than or equal to 3 nucleotides that is of a length great enough to provide the intended function under the expected condition. For example, "sufficient length" means that the binding sequence of an antisense nucleic acid is long enough to provide stable binding to a target site under the expected binding conditions.

The term "stably interact" as used herein, refers to the interaction of nucleic acid molecules of the invention with a target nucleic acid (e.g., by forming hydrogen bonds with complementary nucleotides in the target under physiological conditions). The interaction is stable either alone or in conjunction with $(Y)_n$ and $(Z)_p$ where applicable.

The term "chimeric nucleic acid molecule" or "chimeric oligonucleotide" as used herein, refers to a nucleic acid molecule that can be comprised of both modified or unmodified DNA or RNA.

The term "cap structure" as used herein, refers to chemical modifications, which have been incorporated at either terminus of the oligonucleotide (see for example Wincott et al., WO 97/26270, incorporated by reference herein). These terminal modifications protect the nucleic acid molecule from exonuclease degradation, and can help in delivery and/or localization within a cell. The cap can be present at the 5'-terminus (5'-cap) or at the 3'-terminus (3'-cap) or can be present on both terminus. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, incorporated by reference herein).

In one embodiment the cap structure includes, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, *Tetrahedron* 49, 1925; incorporated by reference herein).

In another embodiment (X)m, (X)o, (X)q, (Y)n and/or (Z)p independently include modifications selected from a group comprising 2'-O-alkyl (e.g. 2'-O-allyl; Sproat et al., supra); 2'-O-alkylthioalkyl (e.g. 2'-O-methylthiomethyl; Karpeisky et al., 1998, Nucleosides & Nucleotides 16, 955–958); L-nucleotides (Tazawa et al., 1970, Biochemistry 3499; Ashley, 1992, J. Am. Chem. Soc. 114, 9731; Klubmann et al., 1996, Nature Biotech 14, 1112); 2'-C-alkyl (Beigelman et al., 1995,J. Biol. Chem. 270, 25702); 1–5-Anhydrohexitol; 2,6-diaminopurine (Strobel et al., 1994, Biochem. 33, 13824–13835); 2'-(N-alanyl) amino-2'-deoxynucleotide; 2'-(N-beta-alanyl) amino; 2'-deoxy-2'-(lysyl) amino; 2'-O-amino (Karpeisky et al., 1995, Tetrahedron Lett. 39, 1131); 2'-deoxy-2'-(N-histidyl) amino; 5-methyl (Strobel, supra); 2'-(N-b-carboxamidine-beta-alanyl) amino; 2'-deoxy-2'-(N-beta-alanyl) (Matulic-Adamic et al., 1995, Bioorg. & Med. Chem. Lett. 5,2721–2724); xylofuranosyl (Rosemeyer et al., 1991, Helvetica Chem. Acta, 74, 748; Seela et al., 1994, Helvetica Chem. Acta, 77, 883; Seela et al., 1996, Helvetica Chem. Acta, 79, 1451).

In another embodiment, the invention features a nucleic acid molecule of any of formula I–VII, where each X and/or Z, independently include a nucleotide modification having formula IX:

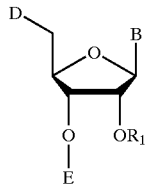

Wherein, each B is independently a modified or an unmodified nucleic acid base; R1 is independently a fluoroalkyl or an alkylthiofluoroalkyl; E is independently a phosphorus-containing group; and D is independently an O, blocking group or a phosphorus-containing group.

In another embodiment, the invention features a nucleic acid molecule of any of formula I–VII, where each X and/or Z, independently include a nucleotide modification having formula X:

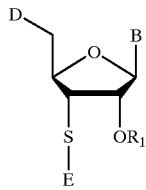

Wherein, each B is independently a modified or an unmodified nucleic acid base; R1 is independently an aklyl, an alkylthioalkyl, a fluoroalkyl or an alkylthiofluoroalkyl; E is independently a phosphorus-containing group; and D is independently an O, blocking group or a phosphorus-containing group.

The term "alkyl" as used herein refers to a saturated aliphatic hydrocarbon, including straight-chain, branched-chain "isoalkyl", and cyclic alkyl groups. The term "alkyl" also comprises alkoxy, alkyl-thio, alkyl-thio-alkyl, alkoxyalkyl, alkylamino, alkenyl, alkynyl, alkoxy, cycloalkenyl, cycloalkyl, cycloalkylalkyl, heterocycloalkyl, heteroaryl, C1–C6 hydrocarbyl, aryl or substituted aryl groups. Preferably, the alkyl group has 1 to 12 carbons. More preferably it is a lower alkyl of from about 1 to 7 carbons, more preferably about 1 to 4 carbons. The alkyl group can be substituted or unsubstituted. When substituted the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, C1–C6 hydrocarbyl, aryl or substituted aryl groups. The term "alkyl" also includes alkenyl groups containing at least one carbon—carbon double bond, including straight-chain, branched-chain, and cyclic groups. Preferably, the alkenyl group has about 2 to 12 carbons. More preferably it is a lower alkenyl of from about 2 to 7 carbons, more preferably about 2 to 4 carbons. The alkenyl group can be substituted or unsubstituted. When substituted the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, C1–C6 hydrocarbyl, aryl or substituted aryl groups. The term "alkyl" also includes alkynyl groups containing at least one carbon—carbon triple bond, including straight-chain, branched-chain, and cyclic groups. Preferably, the alkynyl group has about 2 to 12 carbons. More preferably it is a lower alkynyl of from about 2 to 7 carbons, more preferably about 2 to 4 carbons. The alkynyl group can be substituted or unsubstituted. When substituted the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, C1–C6 hydrocarbyl, aryl or substituted aryl groups. Alkyl groups or moieties of the invention can also include aryl, alkylaryl, carbocyclic aryl, heterocyclic aryl, amide and ester groups. The preferred substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from about 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to an —C(O)—NH—R, where R is either alkyl, aryl, alkylaryl or hydrogen. An "ester" refers to an —C(O)—OR', where R is either alkyl, aryl, alkylaryl or hydrogen.

The term "alkoxyalkyl" as used herein refers to an alkyl-O-alkyl ether, for example methoxyethyl or ethoxymethyl.

The term "alkyl-thio-alkyl" as used herein refers to an alkyl-S-alkyl thioether, for example methylthiomethyl or methylthioethyl.

The term "amino" as used herein refers to a nitrogen containing group as is known in the art derived from ammonia by the replacement of one or more hydrogen radicals by organic radicals. For example, the terms "aminoacyl" and "aminoalkyl" refer to specific N-substituted organic radicals with acyl and alkyl substituent groups respectively.

The term "amination" as used herein refers to a process in which an amino group or substituted amine is introduced into an organic molecule.

The term "exocyclic amine protecting moiety" as used herein refers to a nucleobase amino protecting group compatible with oligonucleotide synthesis, for example an acyl or amide group.

The term "alkenyl" as used herein refers to a straight or branched hydrocarbon of a designed number of carbon atoms containing at least one carbon—carbon double bond. Examples of "alkenyl" include vinyl, allyl, and 2-methyl-3-heptene.

The term "alkoxy" as used herein refers to an alkyl group of indicated number of carbon atoms attached to the parent molecular moiety through an oxygen bridge. Examples of alkoxy groups include, for example, methoxy, ethoxy, propoxy and isopropoxy.

The term "alkynyl" as used herein refers to a straight or branched hydrocarbon of a designed number of carbon atoms containing at least one carbon—carbon triple bond. Examples of "alkynyl" include propargyl, propyne, and 3-hexyne.

The term "aryl" as used herein refers to an aromatic hydrocarbon ring system containing at least one aromatic ring. The aromatic ring can optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl and naphthyl.

The term "cycloalkenyl" as used herein refers to a C3–C8 cyclic hydrocarbon containing at least one carbon—carbon double bond. Examples of cycloalkenyl include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "cycloalkyl" as used herein refers to a C3–C8 cyclic hydrocarbon. Examples of cycloalkyl include cyclopropyl, cyclobutyl, cyclopentyl, cyclohexyl, cycloheptyl and cyclooctyl.

The term "cycloalkylalkyl," as used herein, refers to a C3–C7 cycloalkyl group attached to the parent molecular moiety through an alkyl group, as defined above. Examples of cycloalkylalkyl groups include cyclopropylmethyl and cyclopentylethyl.

The terms "halogen" or "halo" as used herein refers to indicate fluorine, chlorine, bromine, and iodine.

The term "heterocycloalkyl," as used herein refers to a non-aromatic ring system containing at least one heteroatom selected from nitrogen, oxygen, and sulfur. The heterocycloalkyl ring can be optionally fused to or otherwise attached to other heterocycloalkyl rings and/or non-aromatic hydrocarbon rings. Preferred heterocycloalkyl groups have from 3 to 7 members. Examples of heterocycloalkyl groups include, for example, piperazine, morpholine, piperidine, tetrahydrofuran, pyrrolidine, and pyrazole. Preferred heterocycloalkyl groups include piperidinyl, piperazinyl, morpholinyl, and pyrolidinyl.

The term "heteroaryl" as used herein refers to an aromatic ring system containing at least one heteroatom selected from nitrogen, oxygen, and sulfur. The heteroaryl ring can be fused or otherwise attached to one or more heteroaryl rings, aromatic or non-aromatic hydrocarbon rings or heterocycloalkyl rings. Examples of heteroaryl groups include, for example, pyridine, furan, thiophene, 5,6,7,8-tetrahydroisoquinoline and pyrimidine. Preferred examples of heteroaryl groups include thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, and benzopyrazolyl.

The term "C1–C6 hydrocarbyl" as used herein refers to straight, branched, or cyclic alkyl groups having 1–6 carbon atoms, optionally containing one or more carbon—carbon double or triple bonds. Examples of hydrocarbyl groups include, for example, methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, vinyl, 2-pentene, cyclopropylmethyl, cyclopropyl, cyclohexylmethyl, cyclohexyl and propargyl. When reference is made herein to C1–C6 hydrocarbyl containing one or two double or triple bonds it is understood that at least two carbons are present in the alkyl for one double or triple bond, and at least four carbons for two double or triple bonds.

A "blocking group" is a group which is able to be removed after polynucleotide synthesis and/or which is compatible with solid phase polynucleotide synthesis.

A "phosphorus containing group" can include phosphorus in forms such as dithioates, phosphoramidites and/or as part of an oligonucleotide.

The term "abasic" as used herein, refers to moieties lacking a base or having other chemical groups in place of a base at the 1' position, for example a 3',3'-linked or 5',5'-linked deoxyabasic ribose derivative (for more details see Wincott et al., International PCT publication No. WO 97/26270).

In one embodiment C' is selected from a group comprising inverted abasic residue, 4',5'-methylene nucleotide; 1-(beta-D-erythrofuranosyl) nucleotide; 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Beigelman et al., International PCT publication No. WO 97/26270, incorporated by reference herein).

In another embodiment C is selected from a group comprising, 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moeity; 5'-5'-inverted abasic moeity; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moeities (for more details see Beaucage and Iyer, 1993, *Tetrahedron* 49, 1925; incorporated by reference herein).

In another embodiment $(Z)_p$ includes a non-nucleotide linker. Thus, in a preferred embodiment, the invention features an enzymatic nucleic acid molecule having one or more non-nucleotide moieties, and having enzymatic activity to cleave an RNA or DNA molecule. Non-nucleotides as can include abasic nucleotide, polyether, polyamine, polyamide, peptide, carbohydrate, lipid, or polyhydrocarbon compounds. Specific examples include those described by Seela and Kaiser, *Nucleic Acids Res.* 1990, 18:6353 and *Nucleic Acids Res.* 1987, 15:3113; Cload and Schepartz, *J. Am. Chem. Soc.* 1991, 113:6324; Richardson and Schepartz, *J. Am. Chem. Soc.* 1991, 113:5109; Ma et al., *Nucleic Acids Res.* 1993, 21:2585 and Biochemistry 1993, 32:1751; Durand et al., *Nucleic Acids Res.* 1990, 18:6353; McCurdy et al., *Nucleosides & Nucleotides* 1991, 10:287; Jschke et al., *Tetrahedron Lett.* 1993, 34:301; Ono et al., *Biochemistry* 1991, 30:9914; Arnold et al., International Publication No. WO 89/02439; Usman et al., International Publication No. WO 95/06731; Dudycz et al., International Publication No. WO 95/11910 and Ferentz and Verdine, *J. Am. Chem. Soc.* 1991, 113:4000, all hereby incorporated by reference herein. A "non-nucleotide" further means any group or compound which can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymine. Thus, in a preferred embodiment, the invention features an enzymatic nucleic acid molecule having one or more non-nucleotide moieties, and having enzymatic activity to cleave an RNA or DNA molecule.

The term "enzymatic nucleic acid molecule" as used herein, refers to a nucleic acid molecule which has complementarity in a substrate binding region to a specified gene target, and also has an enzymatic activity which is active to specifically cleave target RNA. That is, the enzymatic nucleic acid molecule is able to intermolecularly cleave RNA and thereby inactivate a target RNA molecule. These complementary regions (e.g. $(X)_m$, $(X)_o$, $(X)_q$ and $(Y)_n$ in formulae IV–VII) allow sufficient hybridization of the enzymatic nucleic acid molecule to the target RNA and thus permit cleavage. One hundred percent complementarity is preferred, but complementarity as low as 50–75% can also be useful in this invention (see for example Werner and Uhlenbeck, 1995, *Nucleic Acids Research*, 23, 2092–2096; Hammann et al., 1999, *Antisense and Nucleic Acid Drug Dev.*, 9, 25–31). The nucleic acids can be modified at the base, sugar, and/or phosphate groups. The term enzymatic nucleic acid is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity. The specific enzymatic nucleic acid molecules described in the instant application are not limiting in the invention and those skilled in the art will recognize that all that is important in an enzymatic nucleic acid molecule of this invention is that it has a specific substrate binding site which is complementary to one or more of the target nucleic acid regions, and that it have nucleotide sequences within or surrounding that substrate binding site which impart a nucleic acid cleaving and/or ligation activity to the molecule (Cech et al., U.S. Pat. No. 4,987,071; Cech et al., 1988, 260 JAMA 3030).

The term "complementarity" as used herein, refers to the ability of a nucleic acid to form hydrogen bond(s) with another RNA sequence by either traditional Watson-Crick or other non-traditional types. In reference to the nucleic molecules of the present invention, the binding free energy for a nucleic acid molecule with its target or complementary sequence is sufficient to allow the relevant function of the nucleic acid to proceed, e.g., enzymatic nucleic acid cleavage, antisense or triple helix inhibition. Determination of binding free energies for nucleic acid molecules is well known in the art (see, e.g., Turner et al., 1987, *CSH Symp. Quant. Biol.* LII pp.123–133; Frier et al., 1986, *Proc. Nat. Acad. Sci. USA* 83:9373–9377; Turner et al., 1987, *J. Am. Chem. Soc.* 109:3783–3785). A percent complementarity indicates the percentage of contiguous residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence.

The term "oligonucleotide" as used herein, refers to a molecule comprising two or more nucleotides.

The term "enzymatic portion" as used herein, refers to that part of the enzymatic nucleic acid molecule essential for cleavage of a nucleic acid substrate.

The terms "substrate binding region", "substrate binding arm" or "substrate binding domain" as used herein, refers to that portion/region of a nucleic acid, for example an antisense nucleic acid or enzymatic nucleic acid molecule, which is able to interact, for example via complementarity (i.e., able to base-pair with), with a portion of its substrate. Preferably, such complementarity is 100%, but can be less if desired. For example, as few as 10 bases out of 14 can be base-paired (see for example Werner and Uhlenbeck, 1995, *Nucleic Acids Research,* 23, 2092–2096; Hammann et al., 1999, *Antisense and Nucleic Acid Drug Dev.,* 9, 25–31). Examples of such arms are shown generally in FIGS. 1–4. That is, these arms contain sequences within a enzymatic nucleic acid which are intended to bring enzymatic nucleic acid and target RNA together through complementary base-pairing interactions. The enzymatic nucleic acid of the invention can have binding arms that are contiguous or non-contiguous and can be of varying lengths. The length of the binding arm(s) are preferably greater than or equal to three nucleotides and of sufficient length to stably interact with the target RNA; preferably 12–100 nucleotides; more preferably 14–24 nucleotides long (see for example Werner and Uhlenbeck, supra; Hamman et al., supra; Hampel et al., EP0360257; Berzal-Herranz et al., 1993, *EMBO J.,* 12, 2567–73). If two binding arms are chosen, the design is such that the length of the binding arms are symmetrical (i.e., each of the binding arms is of the same length; e.g., five and five nucleotides, or six and six nucleotides, or seven and seven nucleotides long) or asymmetrical (i.e., the binding arms are of different length; e.g., six and three nucleotides; three and six nucleotides long; four and five nucleotides long; four and six nucleotides long; four and seven nucleotides long; and the like).

The term "RNA" as used herein, refers to a molecule comprising at least one ribonucleotide residue. By "ribonucleotide" or "2'-OH" is meant a nucleotide with a hydroxyl group at the 2' position of a β-D-ribo-furanose moiety.

The term "Inozyme" or "NCH" motif or configuration as used herein, refers to an enzymatic nucleic acid molecule comprising a motif as is generally described as NCH Rz in FIG. 1. Inozymes possess endonuclease activity to cleave RNA substrates having a cleavage triplet NCH/, where N is a nucleotide, C is cytidine and H is adenosine, uridine or cytidine, and / represents the cleavage site. H is used interchangeably with X. Inozymes can also possess endonuclease activity to cleave RNA substrates having a cleavage triplet NCN/, where N is a nucleotide, C is cytidine, and / represents the cleavage site. "I" in FIG. 1 represents an Inosine nucleotide, preferably a ribo-Ino sine or xylo-Ino sine nucleoside.

The term "G-cleaver" motif or configuration as used herein, refers to an enzymatic nucleic acid molecule comprising a motif as is generally described as G-cleaver Rz in FIG. 1. G-cleavers possess endonuclease activity to cleave RNA substrates having a cleavage triplet NYN/, where N is a nucleotide, Y is uridine or cytidine and / represents the cleavage site. G-cleavers can be chemically modified as is generally shown in FIG. 1.

The term "amberzyme" motif or configuration as used herein, refers to an enzymatic nucleic acid molecule comprising a motif as is generally described in FIG. 2. Amberzymes possess endonuclease activity to cleave RNA substrates having a cleavage triplet NG/N, where N is a nucleotide, G is guanosine, and / represents the cleavage site. Amberzymes can be chemically modified to increase nuclease stability through substitutions as are generally shown in FIG. 2. In addition, differing nucleoside and/or non-nucleoside linkers can be used to substitute the 5'-gaaa-3' loops shown in the figure. Amberzymes represent a non-limiting example of an enzymatic nucleic acid molecule that does not require a ribonucleotide (2'-OH) group within its own nucleic acid sequence for activity.

The term "zinzyme" motif or configuration as used herein, refers to an enzymatic nucleic acid molecule comprising a motif as is generally described in FIG. 3. Zinzymes possess endonuclease activity to cleave RNA substrates having a cleavage triplet including but not limited to YG/Y, where Y is uridine or cytidine, and G is guanosine and / represents the cleavage site. Zinzymes can be chemically modified to increase nuclease stability through substitutions as are generally shown in FIG. 3, including substituting 2'-O-methyl guanosine nucleotides for guanosine nucleotides. In addition, differing nucleotide and/or non-nucleotide linkers can be used to substitute the 5'-gaaa-2' loop shown in the figure. Zinzymes represent a non-limiting example of an enzymatic nucleic acid molecule that does not require a ribonucleotide (2'-OH) group within its own nucleic acid sequence for activity.

By 'DNAzyme' is meant, an enzymatic nucleic acid molecule that does not require the presence of a 2'-OH group within its own nucleic acid sequence for activity. In particular embodiments the enzymatic nucleic acid molecule can have an attached linker(s) or other attached or associated groups, moieties, or chains containing one or more nucleotides with 2'—OH groups. DNAzymes can be synthesized chemically or expressed endogenously in vivo, by means of a single stranded DNA vector or equivalent thereof. An example of a DNAzyme is shown in FIG. 4 and is generally reviewed in Usman et al., U.S. Pat. No. , 6,159,714; Chartrand et al., 1995, *NAR* 23, 4092; Breaker et al., 1995, *Chem. Bio.* 2, 655; Santoro et al., 1997, *PNAS* 94, 4262; Breaker, 1999, *Nature Biotechnology,* 17, 422–423; and Santoro et. al., 2000, *J. Am. Chem. Soc.,* 122, 2433–39. Additional DNAzyme motifs can be selected for using techniques similar to those described in these references, and hence, are within the scope of the present invention.

The term "nucleic acid molecule" as used herein, refers to a molecule having nucleotides. The nucleic acid can be single, double, or multiple stranded and can comprise modified or unmodified nucleotides or non-nucleotides or various mixtures and combinations thereof.

In one embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

In another embodiment, the nucleic acid molecule of the present invention can form structures including but not limited to antisense, triplexes, 2–5A chimera antisense, or enzymatic nucleic acid (ribozymes).

The term "antisense nucleic acid", as used herein, refers to a non-enzymatic nucleic acid molecule that binds to target RNA by means of RNA—RNA or RNA-DNA or RNA-PNA (protein nucleic acid; Egholm et al., 1993 *Nature* 365, 566) interactions and alters the activity of the target RNA (for a review, see Stein and Cheng, 1993 *Science* 261, 1004 and Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. For a review of current antisense strategies, see Schmajuk et al., 1999, *J Biol. Chem.*, 274, 21783–21789, Delihas et al., 1997, *Nature*, 15, 751–753, Stein et al., 1997, *Antisense N. A. Drug Dev.*, 7, 151, Crooke, 2000, *Methods Enzymol.*, 313, 3–45; Crooke, 1998, *Biotech. Genet. Eng. Rev.*, 15, 121–157, Crooke, 1997, *Ad. Pharmacol.*, 40, 1–49. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof.

The term "RNase H activating region" as used herein, refers to a region (generally greater than or equal to 4–25 nucleotides in length, preferably from 5–11 nucleotides in length) of a nucleic acid molecule capable of binding to a target RNA to form a non-covalent complex that is recognized by cellular RNase H enzyme (see for example Arrow et al., U.S. Pat. No. 5,849,902; Arrow et al., U.S. Pat. No. 5,989,912). The RNase H enzyme binds to the nucleic acid molecule-target RNA complex and cleaves the target RNA sequence. The RNase H activating region comprises, for example, phosphodiester, phosphorothioate (preferably at least four of the nucleotides are phosphorothiote substitutions; more specifically, 4–11 of the nucleotides are phosphorothiote substitutions); phosphorodithioate, 5'-thiophosphate, or methylphosphonate backbone chemistry or a combination thereof. In addition to one or more backbone chemistries described above, the RNase H activating region can also comprise a variety of sugar chemistries. For example, the RNase H activating region can comprise deoxyribose, arabino, fluoroarabino or a combination thereof, nucleotide sugar chemistry. Those skilled in the art will recognize that the foregoing are non-limiting examples and that any combination of phosphate, sugar and base chemistry of a nucleic acid that supports the activity of RNase H enzyme is within the scope of the definition of the RNase H activating region and the instant invention.

The term "2–5A antisense chimera" as used herein, refers to an antisense oligonucleotide containing a 5'-phosphorylated 2'-5'-linked adenylate residue. These chimeras bind to target RNA in a sequence-specific manner and activate a cellular 2–5A-dependent ribonuclease which, in turn, cleaves the target RNA (Torrence et al., 1993 *Proc. Natl. Acad. Sci. USA* 90, 1300; Silverman et al., 2000, *Methods Enzymol.*, 313, 522–533; Player and Torrence, 1998, *Pharmacol. Ther.*, 78, 55–113).

The term "triplex forming oligonucleotides" or "triplex DNA" as used herein, refers to an oligonucleotide that can bind to a double-stranded DNA in a sequence-specific manner to form a triple-strand helix. Formation of such triple helix structure has been shown to inhibit transcription of the targeted gene (Duval-Valentin et al., 1992 *Proc. Natl. Acad. Sci. USA* 89, 504; Fox, 2000, *Curr. Med. Chem.*, 7, 17–37; Praseuth et. al., 2000, *Biochim. Biophys. Acta*, 1489, 181–206).

The term "gene" as used herein, refers to a nucleic acid that encodes an RNA, for example, nucleic acid sequences including but not limited to structural genes encoding a polypeptide.

In another embodiment, the invention features an antisense oligonucleotide which is capable of interacting with the target RNA and sterically blocking translation, where the oligonucleotide has a 5' and a 3' Cap structure and the oligonucleotide can include modifications at the base, sugar or the phosphate groups.

The nucleic acid molecules of the instant invention are also referred to as GeneBloc reagents, which are essentially nucleic acid molecules (eg; ribozymes, antisense) capable of down-regulating gene expression.

Other features and advantages of the invention will be apparent from the following description of the preferred embodiments thereof, and from the claims.

DESCRIPTION OF THE PREFERRED EMBODIMENTS

The drawings will first briefly be described.

Drawings:

FIG. 1 shows examples of chemically stabilized ribozyme motifs. HH Rz, (SEQ ID NO: 6) represents hammerhead ribozyme motif (Usman et al., 1996, Curr. Op. Struct. Bio., 1, 527); NCH Rz (SEQ ID NO: 8) represents the NCH ribozyme motif (Ludwig & Sproat, International PCT Publication No. WO 98/58058); G-Cleaver, (SEQ ID NO: 10) represents G-cleaver ribozyme motif (Kore et al., 1998, Nucleic Acids Research 26, 4116–4120, Eckstein et al., International PCT publication No. WO 99/16871). N or n, represent independently a nucleotide which can be same or different and have complementarity to each other; rI, represents ribo-Inosine nucleotide; arrow indicates the site of cleavage within the target. Position 4 of the HH Rz and the NCH Rz is shown as having 2'-C-allyl modification, but those skilled in the art will recognize that this position can be modified with other modifications well known in the art, so long as such modifications do not significantly inhibit the activity of the ribozyme.

FIG. 2 shows an example of the Amberzyme ribozyme motif (SEQ ID NO: 11) that is chemically stabilized (see for example Beigelman et al., International PCT publication No. WO 99/55857).

FIG. 3 shows an example of the Zinzyme A ribozyme motif (SEQ ID NO: 13) that is chemically stabilized (see for example Beigelman et al., Beigelman et al., International PCT publication No. WO 99/55857).

FIG. 4 shows an example of a DNAzyme motif (SEQ ID NO: 15) described by Santoro et al., 1997, PNAS, 94, 4262.

SYNTHESIS OF NUCLEIC ACID MOLECULES

Synthesis of nucleic acids greater than 100 nucleotides in length can be difficult using automated methods, and the therapeutic cost of such molecules can be prohibitive. In this invention, small nucleic acid motifs ("small refers to nucleic acid motifs less than about 100 nucleotides in length, preferably less than about 80 nucleotides in length, and more preferably less than about 50 nucleotides in length; e.g., antisense oligonucleotides, hammerhead or the NCH ribozymes) are preferably used for exogenous delivery. The simple structure of these molecules increases the ability of the nucleic acid to invade targeted regions of RNA structure.

Exemplary molecules of the instant invention are chemically synthesized, and others can similarly be synthesized.

Oligonucleotides (eg; antisense, GeneBlocs) are synthesized using protocols known in the art as described in Caruthers et al, 1992, *Methods in Enzymology* 211, 3–19, Thompson et al., International PCT Publication No. WO 99/54459, Wincott et al., 1995, *Nucleic Acids Res.* 23, 2677–2684, Wincott et al., 1997, *Methods Mol. Bio.*, 74, 59, Brennan et al., 1998, *Biotechnol Bioeng.*, 61, 33–45, and Brennan, U.S. Pat. No. 6,001,311. All of these references are incorporated herein by reference. The synthesis of oligonucleotides makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 µmol scale protocol with a 2.5 min coupling step for 2'-O-methylated nucleotides and a 45 sec coupling step for 2'-deoxy nucleotides. Table II outlines the amounts and the contact times of the reagents used in the synthesis cycle. Alternatively, syntheses at the 0.2 µmol scale can be performed on a 96-well plate synthesizer, such as the instrument produced by Protogene (Palo Alto, Calif.) with minimal modification to the cycle. A 33-fold excess (60 µL of 0.11 M=6.6 µmol) of 2'-O-methyl phosphoramidite and a 105-fold excess of S-ethyl tetrazole (60 µL of 0.25 M=15 µmol) can be used in each coupling cycle of 2'-O-methyl residues relative to polymer-bound 5'-hydroxyl. A 22-fold excess (40 µL of 0.11 M=4.4 µmol) of deoxy phosphoramidite and a 70-fold excess of S-ethyl tetrazole (40 µL of 0.25 M=10 µmol) can be used in each coupling cycle of deoxy residues relative to polymer-bound 5'-hydroxyl. Average coupling yields on the 394 Applied Biosystems, Inc. synthesizer, determined by calorimetric quantitation of the trityl fractions, are typically 97.5–99%. Other oligonucleotide synthesis reagents for the 394 Applied Biosystems, Inc. synthesizer include; detritylation solution is 3% TCA in methylene chloride (ABI); capping is performed with 16% N-methyl imidazole in THF (ABI) and 10% acetic anhydride/10% 2,6-lutidine in THF (ABI); and oxidation solution is 16.9 mM $I_2$, 49 mM pyridine, 9% water in THF (PERSEPTIVE™). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide, 0.05 M in acetonitrile) is used.

Deprotection of the antisense oligonucleotides is performed as follows: the polymer-bound trityl-on oligoribonucleotide is transferred to a 4 mL glass screw top vial and suspended in a solution of 40% aq. methylamine (1 mL) at 65° C. for 10 min. After cooling to –20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder.

The method of synthesis used for RNA and chemically modified RNA including certain enzymatic nucleic acid molecules follows the procedure as described in Usman et al., 1987, *J. Am. Chem. Soc.*, 109, 7845; Scaringe et al., 1990, *Nucleic Acids Res.*, 18, 5433; and Wincott et al., 1995, *Nucleic Acids Res.* 23, 2677–2684 Wincott et al., 1997, *Methods Mol. Bio.*, 74, 59, and makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 µmol scale protocol with a 7.5 min coupling step for alkylsilyl protected nucleotides and a 2.5 min coupling step for 2'-O-methylated nucleotides. Table II outlines the amounts and the contact times of the reagents used in the synthesis cycle. Alternatively, syntheses at the 0.2 µmol scale can be done on a 96-well plate synthesizer, such as the instrument produced by Protogene (Palo Alto, Calif.) with minimal modification to the cycle. A 33-fold excess (60 µL of 0.11 M=6.6 µmol) of 2'-O-methyl phosphoramidite and a 75-fold excess of S-ethyl tetrazole (60 µL of 0.25 M=15 µmol) can be used in each coupling cycle of 2'-O-methyl residues relative to polymer-bound 5'-hydroxyl. A 66-fold excess (120 µL of 0.11 M=13.2 µmol) of alkylsilyl (ribo) protected phosphoramidite and a 150-fold excess of S-ethyl tetrazole (120 µL of 0.25 M=30 µmol) can be used in each coupling cycle of ribo residues relative to polymer-bound 5'-hydroxyl. Average coupling yields on the 394 Applied Biosystems, Inc. synthesizer, determined by colorimetric quantitation of the trityl fractions, are typically 97.5–99%. Other oligonucleotide synthesis reagents for the 394 Applied Biosystems, Inc. synthesizer include; detritylation solution is 3% TCA in methylene chloride (ABI); capping is performed with 16% N-methyl imidazole in THF (ABI) and 10% acetic anhydride/10% 2,6-lutidine in THF (ABI); oxidation solution is 16.9 mM $I_2$, 49 mM pyridine, 9% water in THF (PERSEPTIVE™). Burdick & Jackson Synthesis Grade acetonitrile is used directly from the reagent bottle. S-Ethyltetrazole solution (0.25 M in acetonitrile) is made up from the solid obtained from American International Chemical, Inc.

Alternately, for the introduction of phosphorothioate linkages, Beaucage reagent (3H-1,2-Benzodithiol-3-one 1,1-dioxide 0.05 M in acetonitrile) is used.

Deprotection of the RNA is performed using either a two-pot or one-pot protocol. For the two-pot protocol, the polymer-bound trityl-on oligoribonucleotide is transferred to a 4 mL glass screw top vial and suspended in a solution of 40% aq. methylamine (1 mL) at 65° C. for 10 min. After cooling to –20° C., the supernatant is removed from the polymer support. The support is washed three times with 1.0 mL of EtOH:MeCN:H20/3:1:1, vortexed and the supernatant is then added to the first supernatant. The combined supernatants, containing the oligoribonucleotide, are dried to a white powder. The base deprotected oligoribonucleotide is resuspended in anhydrous TEA/HF/NMP solution (300 µL of a solution of 1.5 mL N-methylpyrrolidinone, 750 µL TEA and 1 mL TEA·3HF to provide a 1.4 M HF concentration) and heated to 65° C. After 1.5 h, the oligomer is quenched with 1.5 M $NH_4HCO_3$.

Alternatively, for the one-pot protocol, the polymer-bound trityl-on oligoribonucleotide is transferred to a 4 mL glass screw top vial and suspended in a solution of 33% ethanolic methylamine/DMSO: 1/1 (0.8 mL) at 65° C. for 15 min. The vial is brought to r.t. TEA·3HF (0.1 mL) is added and the vial is heated at 65° C. for 15 min. The sample is cooled at –20° C. and then quenched with 1.5 M $NH_4HCO_3$.

For purification of the trityl-on oligomers, the quenched $NH_4HCO_3$ solution is loaded onto a C-18 containing cartridge that had been prewashed with acetonitrile followed by 50 mM TEAA. After washing the loaded cartridge with water, the RNA is detritylated with 0.5% TFA for 13 min. The cartridge is then washed again with water, salt exchanged with 1 M NaCl and washed with water again. The oligonucleotide is then eluted with 30% acetonitrile.

Inactive hammerhead ribozymes or binding attenuated control (BAC) oligonucleotides can be synthesized by substituting a U for $G_5$ and a U for $A_{14}$ (numbering from Hertel, K. J., et al., 1992, *Nucleic Acids Res.*, 20, 3252). Similarly, one or more nucleotide substitutions can be introduced in other enzymatic nucleic acid molecules to inactivate the molecule and such molecules can serve as a negative control.

The average stepwise coupling yields are typically >98% (Wincott et al., 1995 *Nucleic Acids Res.* 23, 2677–2684). Those of ordinary skill in the art will recognize that the scale of synthesis can be adapted to be larger or smaller than the example described above including but not limited to 96 well format, with the ratio of chemicals being used in the reaction adjusted accordingly.

Alternatively, the nucleic acid molecules of the present invention can be synthesized separately and joined together post-synthetically, for example by ligation (Moore et al., 1992, *Science* 256, 9923; Draper et al., International PCT publication No. WO 93/23569; Shabarova et al., 1991, *Nucleic Acids Research* 19, 4247; Bellon et al., 1997, *Nucleosides & Nucleotides*, 16, 951; Bellon et al., 1997, *Bioconjugate Chem.* 8, 204).

The nucleic acid molecules of the present invention are modified extensively to enhance stability by modification with nuclease resistant groups, for example, 2'-amino, 2'-C-allyl, 2'flouro, 2'-O-methyl, 2'-H (for a review see Usman and Cedergren, 1992, *TIBS* 17, 34; Usman et al., 1994, *Nucleic Acids Symp. Ser.* 31, 163). Ribozymes are purified by gel electrophoresis using general methods or are purified by high pressure liquid chromatography (HPLC; See Wincott et al., Supra, the totality of which is hereby incorporated herein by reference) and are re-suspended in water.

Administration of Nucleic Acid Molecules

Methods for the delivery of nucleic acid molecules are described in Akhtar et al., 1992, *Trends Cell Bio.*, 2, 139; and *Delivery Strategies for Antisense Oligonucleotide Therapeutics*, ed. Akhtar, 1995 which are both incorporated herein by reference. Sullivan et al., PCT WO 94/02595, further describes the general methods for delivery of enzymatic RNA molecules. These protocols can be utilized for the delivery of virtually any nucleic acid molecule. Nucleic acid molecules can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to oral (tablet or pill form) and/or intrathecal delivery (Gold, 1997, *Neuroscience*, 76, 1153–1158). Other approaches include the use of various transport and carrier systems, for example, through the use of conjugates and biodegradable polymers. For a comprehensive review on drug delivery strategies including CNS delivery, see Ho et al., 1999, *Curr. Opin. Mol. Ther.*, 1, 336–343 and Jain, *Drug Delivery Systems: Technologies and Commercial Opportunities*, Decision Resources, 1998 and Groothuis et al., 1997, *J. NeuroVirol.*, 3, 387–400. More detailed descriptions of nucleic acid delivery and administration are provided in Sullivan et al., supra, Draper et al., PCT WO93/23569, Beigelman et al., PCT WO99/05094, and Klimuk et al., PCT WO99/04819 all of which have been incorporated by reference herein.

The molecules of the instant invention can be used as pharmaceutical agents. Pharmaceutical agents prevent, inhibit the occurrence, or treat (alleviate a symptom to some extent, preferably all of the symptoms) of a disease state in a patient.

The negatively charged polynucleotides of the invention can be administered (e.g., RNA, DNA or protein) and introduced into a patient by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as tablets, capsules or elixirs for oral administration; suppositories for rectal administration; sterile solutions; suspensions for injectable administration; and the other compositions known in the art.

The present invention also includes pharmaceutically acceptable formulations of the compounds described. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic administration, into a cell or patient, preferably a human. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

The term "systemic administration" as used herein, refers to in vivo systemic absorption or accumulation of drugs in the blood stream followed by distribution throughout the entire body. Administration routes which lead to systemic absorption include, without limitations: intravenous, subcutaneous, intraperitoneal, inhalation, oral, intrapulmonary and intramuscular. Each of these administration routes expose the desired negatively charged polymers, e.g., nucleic acids, to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful. This approach can provide enhanced delivery of the drug to target cells by taking advantage of the specificity of macrophage and lymphocyte immune recognition of abnormal cells, such as cancer cells.

The terms "pharmaceutically acceptable formulation" or "pharmaceutically acceptable carrier" as used herein, refers to a composition or formulation that allows for the effective distribution of the nucleic acid molecules of the instant invention in the physical location most suitable for their desired activity. Non-limiting examples of agents suitable for formulation with the nucleic acid molecules of the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues, for example the CNS (Jolliet-Riant and Tillement, 1999, Fundam. Clin. Pharmacol., 13, 16–26); biodegradable polymers, such as poly (DL-lactide-coglycolide) microspheres for sustained release delivery after implantation (Emerich, D F et al, 1999, Cell Transplant, 8, 47–58) Alkermes, Inc. Cambridge, Mass.; and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941–949, 1999). Other non-limiting examples of delivery strategies, including CNS delivery of the nucleic acid molecules of the instant invention include material described in Boado et al., 1998, J. Pharm. Sci., 87, 1308–1315; Tyler et al., 1999, FEBS Lett., 421, 280–284; Pardridge et al., 1995, PNAS USA., 92, 5592–5596; Boado, 1995, Adv. Drug Delivery Rev., 15, 73–107; Aldrian-Herrada et al., 1998, Nucleic Acids Res., 26, 4910–4916; and Tyler et al., 1999, PNAS USA., 96, 7053–7058. All these references are hereby incorporated herein by reference.

The invention also features the use of the composition comprising surface-modified liposomes containing poly (ethylene glycol) lipids (PEG-modified, or long-circulating liposomes or stealth liposomes). Nucleic acid molecules of the invention can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601–2627; Ishiwata et al., Chem. Pharm. Bull. 1995, 43, 1005–1011). Such liposomes have been shown to accumulate selectively in tumors, presumably by extravasation and capture in the neovascularized target tissues (Lasic et al., Science 1995, 267, 1275–1276; Oku et al., 1995, Biochim. Biophys. Acta, 1238, 86–90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864–24870; Choi et al., International PCT Publication No. WO 96/10391; Ansell et al., International PCT Publication No. WO 96/10390; Holland et al., International PCT Publication No. WO 96/10392; all of which are incorporated by reference herein). Long-circulating liposomes are also likely to protect drugs from nuclease degradation to a greater extent compared to cationic liposomes, based on their ability to avoid accumulation in metabolically aggressive MPS tissues such as the liver and spleen. All of these references are incorporated by reference herein.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences,* Mack Publishing Co. (A. R. Gennaro edit. 1985) hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 100 mg/kg body weight/day of active ingredients is administered dependent upon potency of the negatively charged polymer.

The nucleic acid molecules of the invention and formulations thereof can be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions containing nucleic acid molecules of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono-or diglycerides. In addition, fatty acids such as oleic acid find use in the preparation of injectables.

The nucleic acid molecules of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that can be combined with the carrier materials to produce a single dosage form varies depending upon the host treated and the particular mode of administration. Dosage unit forms generally contain between from about 1 mg to about 500 mg of an active ingredient.

It is understood that the specific dose level for any particular patient depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The nucleic acid molecules of the present invention can also be administered to a patient in combination with other therapeutic compounds to increase the overall therapeutic effect. The use of multiple compounds to treat an indication can increase the beneficial effects while reducing the presence of side effects.

In yet another aspect the invention features an expression vector comprising nucleic acid sequence encoding at least one of the catalytic nucleic acid molecule of the invention, in a manner which allows expression of that nucleic acid molecule. The expression vector comprises in one embodiment; a) a transcription initiation region; b) a transcription termination region; c) a gene encoding at least one said nucleic acid molecule; and wherein said gene is operably linked to said initiation region and said termination region, in a manner which allows expression and/or delivery of said nucleic acid molecule. In another preferred embodiment the expression vector comprises: a) a transcription initiation region; b) a transcription termination region; c) an open reading frame; d) a gene encoding at least one said nucleic acid molecule, wherein said gene is operably linked to the 3'-end of said open reading frame; and wherein said gene is operably linked to said initiation region, said open reading frame and said termination region, in a manner which allows expression and/or delivery of said nucleic acid molecule. In yet another embodiment the expression vector comprises: a) a transcription initiation region; b) a transcription termination region; c) an intron; d) a gene encoding at least one said nucleic acid molecule; and wherein said gene is operably linked to said initiation region, said intron and said termination region, in a manner which allows expression and/or delivery of said nucleic acid molecule. In another embodiment, the expression vector comprises: a) a transcription initiation region; b) a transcription termination region; c) an intron; d) an open reading frame; e) a gene encoding at least one said nucleic acid molecule, wherein said gene is operably linked to the 3'-end of said open reading frame; and wherein said gene is operably linked to said initiation region, said intron, said open reading frame and said termination region, in a manner which allows expression and/or delivery of said nucleic acid molecule.

Mechanism of Action of Nucleic Acid Molecules of the Invention

Antisense:

Antisense molecules can be modified or unmodified RNA, DNA, or mixed polymer oligonucleotides and primarily function by specifically binding to matching sequences resulting in inhibition of peptide synthesis (Wu-Pong, Nov 1994, BioPharm, 20–33). The antisense oligonucleotide binds to target RNA by Watson Crick base-pairing and blocks gene expression by preventing ribosomal translation of the bound sequences either by steric blocking or by activating RNase H enzyme. Antisense molecules can also alter protein synthesis by interfering with RNA processing or transport from the nucleus into the cytoplasm (Mukhopadhyay & Roth, 1996, Crit. Rev. in Oncogenesis 7, 151–190).

In addition, binding of single stranded DNA to RNA can result in nuclease degradation of the heteroduplex (Wu-Pong, supra; Crooke, supra). To date, the only backbone modified DNA chemistry which will act as substrates for RNase H are phosphorothioates, phosphorodithioates, and borontrifluoridates. Recently it has been reported that 2'-arabino and 2'-fluoro arabino-containing oligos can also activate RNase H activity.

A number of antisense molecules have been described that utilize novel configurations of chemically modified nucleotides, secondary structure, and/or RNase H substrate domains (Woolf et al., International PCT Publication No. WO 98/13526; Thompson et al., International PCT Publication No. WO 99/54459; Hartmann et al., U.S. Ser. No. 60/101,174 which was filed on Sep. 21, 1998) all of these are incorporated by reference herein in their entirety.

In addition, antisense deoxyoligoribonucleotides can be used to target RNA by means of DNA-RNA interactions, thereby activating RNase H, which digests the target RNA in the duplex. Antisense DNA can be expressed via the use of a single stranded DNA intracellular expression vector or equivalents and variations thereof.

Triplex Forming Oligonucleotides (TFO):

Single stranded DNA can be designed to bind to genomic DNA in a sequence specific manner. TFOs are comprised of pyrimidine-rich oligonucleotides which bind DNA helices through Hoogsteen Base-pairing (Wu-Pong, supra). The resulting triple helix composed of the DNA sense, DNA antisense, and TFO disrupts RNA synthesis by RNA polymerase. The TFO mechanism can result in gene expression or cell death since binding can be irreversible (Mukhopadhyay & Roth, supra).

2–5A Antisense Chimera:

The 2–5A system is an interferon mediated mechanism for RNA degradation found in higher vertebrates (Mitra et al., 1996, Proc Nat Acad Sci USA 93, 6780–6785). Two types of enzymes, 2–5A synthetase and RNase L, are required for RNA cleavage. The 2–5A synthetases require double stranded RNA to form 2'-5' oligoadenylates (2–5A). 2–5A then acts as an allosteric effector for utilizing RNase L which has the ability to cleave single stranded RNA. The ability to form 2–5A structures with double stranded RNA makes this system particularly useful for inhibition of viral replication.

(2'-5') oligoadenylate structures can be covalently linked to antisense molecules to form chimeric oligonucleotides capable of RNA cleavage (Torrence, supra). These molecules putatively bind and activate a 2–5A dependent RNase, the oligonucleotide/enzyme complex then binds to a target RNA molecule which can then be cleaved by the RNase enzyme.

Enzymatic Nucleic Acid:

Several varieties of naturally-occurring enzymatic RNAs are presently known, for example see Table I. In addition, several in vitro selection (evolution) strategies (Orgel, 1979, Proc. R. Soc. London, B 205, 435) have been used to evolve new nucleic acid catalysts capable of catalyzing cleavage and ligation of phosphodiester linkages (Joyce, 1989, Gene, 82, 83–87; Beaudry et al., 1992, Science 257, 635–641; Joyce, 1992, Scientific American 267, 90–97; Breaker et al., 1994, TIBTECH 12, 268; Bartel et al., 1993, Science 261:1411–1418; Szostak, 1993, TIBS 17, 89–93; Kumar et al., 1995, FASEB J., 9, 1183; Breaker, 1996, Curr. Op. Biotech., 7, 442; Santoro et al., 1997, Proc. Natl. Acad. Sci., 94, 4262; Tang et al., 1997, RNA 3, 914; Nakamaye & Eckstein, 1994, supra; Long & Uhlenbeck, 1994, supra; Ishizaka et al., 1995, supra; Vaish et al., 1997, Biochemistry 36, 6495; all of these are incorporated by reference herein). Each can catalyze a series of reactions including the hydrolysis of phosphodiester bonds in trans (and thus can cleave other RNA molecules) under physiological conditions.

The enzymatic nature of an enzymatic nucleic acid molecule can allow the concentration of enzymatic nucleic acid molecule necessary to affect a therapeutic treatment to be lower. This reflects the ability of the enzymatic nucleic acid molecule to act enzymatically. Thus, a single enzymatic nucleic acid molecule is able to cleave many molecules of target RNA. In addition, the enzymatic nucleic acid molecule is a highly specific inhibitor, with the specificity of inhibition depending not only on the base-pairing mechanism of binding to the target RNA, but also on the mechanism of target RNA cleavage. Single mismatches, or base-substitutions, near the site of cleavage can be chosen to greatly attenuate the catalytic activity of a enzymatic nucleic acid molecule.

Nucleic acid molecules having an endonuclease enzymatic activity are able to repeatedly cleave other separate RNA molecules in a nucleotide base sequence-specific manner. Such enzymatic nucleic acid molecules can be targeted to virtually any RNA transcript, and achieve efficient cleavage in vitro (Zaug et al., 324, Nature 429 1986; Uhlenbeck, 1987 Nature 328, 596; Kim et al, 84 Proc. Natl. Acad. Sci. USA 8788, 1987; Dreyfus, 1988, Einstein Quart. J. Bio. Med., 6, 92; Haseloff and Gerlach, 334 Nature 585, 1988; Cech, 260 JAMA 3030, 1988; and Jefferies et al., 17 Nucleic Acids Research 1371, 1989; Santoro et al., 1997 supra).

Because of their sequence specificity, trans-cleaving enzymatic nucleic acid molecules can be used as therapeutic agents for human disease (Usman & McSwiggen, 1995 Ann. Rep. Med. Chem. 30, 285–294; Christoffersen and Marr, 1995 J. Med. Chem. 38, 2023–2037). Enzymatic nucleic acid molecules can be designed to cleave specific RNA targets within the background of cellular RNA. Such a cleavage event renders the RNA non-functional and abrogates protein expression from that RNA. In this manner, synthesis of a protein associated with a disease state can be selectively inhibited (Warashina et al., 1999, Chemistry and Biology, 6, 237–250).

Optimizing Nucleic Acid Activity

Chemically synthesizing nucleic acid molecules with modifications (base, sugar and/or phosphate) that prevent their degradation by serum ribonucleases can increase their potency (see e.g., Eckstein et al., International Publication No. WO 92/07065; Perrault et al., 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of the nucleic acid molecules herein). Modifications which enhance their efficacy in cells, and removal of bases from nucleic acid molecules to shorten oligonucleotide synthesis times and reduce chemical requirements are desired. (All these publications are hereby incorporated by reference herein).

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-flouro, 2'-O-methyl, 2'-H, nucleotide base modifications (for a review see Usman and Cedergren, 1992, *TIBS.* 17, 34; Usman et al., 1994, *Nucleic Acids Symp. Ser.* 31, 163; Burgin et al, 1996, *Biochemistry,* 35, 14090). Sugar modification of nucleic acid molecules have been extensively described in the art (see Eckstein et al., International Publication PCT No. WO 92/07065; Perrault et al. *Nature,* 1990, 344, 565–568; Pieken et al. *Science,* 1991, 253, 314–317; Usman and Cedergren, *Trends in Biochem. Sci.,* 1992, 17, 334–339; Usman et al. International Publication PCT No. WO 93/15187; Sproat, U.S. Pat. No. 5,334,711 and Beigelman et al., 1995, *J Biol. Chem.,* 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, *Tetrahedron Lett.,* 39, 1131; Earnshaw and Gait, 1998, *Biopolymers (Nucleic acid Sciences),* 48, 39–55; Verma and Eckstein, 1998, *Annu. Rev. Biochem.,* 67, 99–134; and Burlina et al., 1997, *Bioorg. Med. Chem.,* 5, 1999–2010; all of the references are hereby incorporated in their totality by reference herein). Such publications describe general methods and strategies to determine the location of incorporation of sugar, base and/or phosphate modifications and the like into ribozymes without inhibiting catalysis, and are incorporated by reference herein. In view of such teachings, similar modifications can be used as described herein to modify the nucleic acid molecules of the instant invention.

While chemical modification of oligonucleotide internucleotide linkages with phosphorothioate, phosphorothioate, and/or 5'-methylphosphonate linkages improves stability, too many of these modifications can cause some toxicity. Therefore when designing nucleic acid molecules the amount of these internucleotide linkages should be minimized. The reduction in the concentration of these linkages should lower toxicity resulting in increased efficacy and higher specificity of these molecules.

Nucleic acid molecules having chemical modifications that maintain or enhance activity are provided. Such nucleic acid is also generally more resistant to nucleases than unmodified nucleic acid. Thus, in a cell and/or in vivo the activity can not be significantly lowered. Therapeutic nucleic acid molecules delivered exogenously are optimally stable within cells until translation of the target RNA has been inhibited long enough to reduce the levels of the undesirable protein. This period of time varies between hours to days depending upon the disease state. Nucleic acid molecules are preferably resistant to nucleases in order to function as effective intracellular therapeutic agents. Improvements in the chemical synthesis of RNA and DNA (Wincott et al., 1995 *Nucleic Acids Res.* 23, 2677; Caruthers et al., 1992, *Methods in Enzymology* 211,3–19 (incorporated by reference herein) have expanded the ability to modify nucleic acid molecules by introducing nucleotide modifications to enhance their nuclease stability as described above.

Use of the nucleic acid-based molecules of the invention can lead to better treatment of the disease progression by affording the possibility of combination therapies (e.g., multiple antisense or enzymatic nucleic acid molecules targeted to different genes, nucleic acid molecules coupled with known small molecule inhibitors, or intermittent treatment with combinations of molecules (including different motifs) and/or other chemical or biological molecules). The treatment of patients with nucleic acid molecules can also include combinations of different types of nucleic acid molecules.

Therapeutic nucleic acid molecules (e.g., enzymatic nucleic acid molecules and antisense nucleic acid molecules) delivered exogenously are optimally stable within cells until translation of the target RNA has been inhibited long enough to reduce the levels of the undesirable protein. This period of time varies between hours to days depending upon the disease state. These nucleic acid molecules should be resistant to nucleases in order to function as effective intracellular therapeutic agents. Improvements in the chemical synthesis of nucleic acid molecules described in the instant invention and in the art have expanded the ability to modify nucleic acid molecules by introducing nucleotide modifications to enhance their nuclease stability as described above.

In one embodiment, nucleic acid catalysts having chemical modifications that maintain or enhance enzymatic activity are provided. Such nucleic acids are also generally more resistant to nucleases than unmodified nucleic acid. Thus, in a cell and/or in vivo the activity of the nucleic acid can not be significantly lowered. As exemplified herein such enzymatic nucleic acids are useful in a cell and/or in vivo even if activity over all is reduced about 10 fold (Burgin et al., 1996, *Biochemistry,* 35, 14090). Such enzymatic nucleic acids herein are said to "maintain" the enzymatic activity of an all RNA ribozyme or all DNA DNAzyme.

By "enhanced enzymatic activity" is meant to include activity measured in cells and/or in vivo where the activity is a reflection of both catalytic activity and ribozyme stability. In this invention, the product of these properties is increased or not significantly (less that 10 fold) decreased in vivo compared to an all RNA ribozyme.

Target Validation

One of the most challenging tasks in drug discovery is the choice of a therapeutic target. Historically, traditional biochemical and other studies have offered limited information in this regard. However, recent advances in genomics offer the potential to revolutionize both the speed and certainty of therapeutic target identification. Progress in characterizing the genes in the human genome has been very rapid, and it is now estimated that the entire complement of genes in the human genome can be sequenced before the end of this century. However, this mass of information is coming to the scientific world without a road map. Converting pure gene sequence information into a functional understanding of their role in human disease is proving to be a much more difficult problem. Even after a group of genes is associated with a particular disease, the process of validating which genes are appropriate for use as therapeutic targets is often slow and costly. Most companies with genomics activities now have access to myriad partial or full sequences, but do not possess adequate technologies to determine which of those sequences is an appropriate therapeutic target. As a result, only a few genes have been unequivocally identified as the causative agent for a specific disease.

The nucleic acid molecules of the present invention can inhibit gene expression in a highly specific manner by binding to and causing the cleavage of the mRNA corresponding to the gene of interest, and thereby prevent production of the gene product (Christoffersen, Nature Biotech, 1997, 2, 483–484). Appropriate delivery vehicles can be combined with these nucleic acid molecules (including polymers, cationic lipids, liposomes and the like) and delivered to appropriate cell culture or in vivo animal disease models as described above. By monitoring inhibition of gene expression and correlation with phenotypic results, the relative importance of the particular gene sequence to disease pathology can be established. The process can be both fast and highly selective, and allow for the process to be used at any point in the development of the organism. The novel chemical composition of these nucleic acid molecules can allow for added stability and therefore increased efficacy.

EXAMPLES

The following are non-limiting examples demonstrating the utility of the nucleic acid molecules of the instant invention. Those in the art will recognize that certain experimental conditions such as temperatures, reaction times, media conditions, transfection reagents and RNA assays are not meant to be limiting and can be readily modified without significantly altering the protocols.

Example 1

Administration of GeneBlocs in vivo.

GeneBlocs (SEQ ID NOS: 1–4, Table III) were designed, synthesized, and were tested in the rat corneal model of VEGF-induced angiogenesis (Nucleic Acid Res., vol. 27: 2569, 1999). Briefly, a filter paper disk soaked in VEGF (1 $\mu$l of a 30 $\mu$M solution in 82 mM Tris-HCl, pH 6.9) was implanted in a stromal pocket in the eye of an anesthesized male Sprague-Dawley rat, 1 mm from the edge of the corneal limbus. After implantation of the disk, vehicle control (600 nl sterile water), mismatch control (SEQ ID NO: 2 or SEQ ID NO: 4) (10 $\mu$g in 600 nl sterile water), or active GeneBloc (SEQ ID NO: 1 or SEQ ID NO: 3) (10 $\mu$g in 600 nl sterile water) was administered by intraconjunctival injection adjacent to the disk implant site, 1 mm from the edge of the corneal limbus. Further control treatments included implantation of Tris-soaked disks and injection of vehicle, and for specificity control basic FGF-soaked disks and injection of active GeneBloc. Five days after surgical implantation of the disks, animals were euthanized and cornea were digitally imaged for quantitation of neovascular surface area using computerized morphometry.

Animal Guidelines and Anesthesia.

Animal housing and experimentation adhered to standards outlined in the 1996 Guide for the Care and Use of Laboratory Animals (National Research Council). Male Sprague Dawley rats (250–300 g) were anesthetized with ketamine (50 mg/kg), xylazine (10 mg/kg), and acepromazine (0.5 mg/kg) administered intramuscularly (im). The level of anesthesia was monitored every 2–3 min by applying hind limb paw pressure and examining for limb withdrawal. Atropine (0.4 mg/kg, im) was also administered to prevent potential corneal reflex-induced bradycardia.

Preparation of VEGF Soaked Disk.

For corneal implantation, 0.57 mm diameter nitrocellulose disks, prepared from 0.45 $\mu$m pore diameter nitrocellulose filter membranes (Millipore Corporation), were soaked for 30 min in 1 $\mu$L of 30 $\mu$M VEGF$_{165}$ in 82 mM Tris HCl (pH 6.9) in covered petri dishes on ice.

Corneal Surgery.

The rat corneal model used in this study was a modified from Koch et al. Supra and Pandey et al., supra. Briefly, corneas were irrigated with 0.5% povidone iodine solution followed by normal saline and two drops of 2% lidocaine. Under a dissecting microscope (Leica MZ-6), a stromal pocket was created and a presoaked filter disk (see above) was inserted into the pocket such that its edge was 1 mm from the corneal limbus.

Intraconjunctival Injection of Test Solutions.

Immediately after disk insertion, the tip of a 40–50 $\mu$m OD injector was inserted within the conjunctival tissue 1 mm away from the edge of the corneal limbus that was directly adjacent to the VEGF-soaked filter disk. Six hundred nanoliters of test solution (ribozyme, attenuated control or sterile water vehicle) were dispensed at a rate of 1.2 $\mu$L/min using a syringe pump (Kd Scientific). The injector was then removed, serially rinsed in 70% ethanol and sterile water and immersed in sterile water between each injection. Once the test solution was injected, closure of the eyelid was maintained using microaneurism clips until the animal began to recover gross motor activity. Following treatment, animals were warmed on a heating pad at 37° C.

Diagnostic Uses

Nucleic acid molecules of this invention can be used as diagnostic tools to examine genetic drift and mutations within diseased cells or to detect the presence of specific RNAs in a cell. The close relationship between for example ribozyme activity and the structure of the target RNA allows the detection of mutations in any region of the molecule which alters the base-pairing and three-dimensional structure of the target RNA. By using multiple ribozymes described in this invention, one can map nucleotide changes which are important to RNA structure and function in vitro, as well as in cells and tissues. Cleavage of target RNAs with ribozymes can be used to inhibit gene expression and define the role (essentially) of specified gene products in the progression of disease. In this manner, other genetic targets can be defined as important mediators of the disease. These experiments will lead to better treatment of the disease progression by affording the possibility of combinational therapies (e.g., multiple nucleic acid molecules targeted to different genes, nucleic acid molecules coupled with known small molecule inhibitors, or intermittent treatment with combinations of nucleic acid molecules and/or other chemical or biological molecules). Other in vitro uses of nucleic acid molecules of this invention are well known in the art, and include detection of the presence of RNAs related to various conditions. Such RNA is detected by determining the presence of a cleavage product after treatment with for example, an enzymatic nucleic acid molecule using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of a phenotype is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Additional Uses

Potential uses of sequence-specific enzymatic nucleic acid molecules of the instant invention can have many of the same applications for the study of RNA that DNA restriction endonucleases have for the study of DNA (Nathans et al., 1975 *Ann. Rev. Biochem.* 44:273). For example, the pattern of restriction fragments can be used to establish sequence relationships between two related RNAs, and large RNAs can be specifically cleaved to fragments of a size more useful for study. The ability to engineer sequence specificity of the enzymatic nucleic acid molecule is ideal for cleavage of RNAs of unknown sequence. Applicant has described the use of nucleic acid molecules to down-regulate gene expression of target genes in bacterial, microbial, fungal, viral, and eukaryotic systems including plant, or mammalian cells.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims.

The invention illustratively described herein suitably can be practiced in the absence of any element or elements, limitation or limitations which is not specifically disclosed herein. Thus, for example, in each instance herein any of the terms "comprising", "consisting essentially of" and "consisting of" can be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed can be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Other embodiments are within the claims that follow.

TABLE I

Characteristics of naturally occurring ribozymes

Group I Introns

Size: ~150 to >1000 nucleotides.
Requires a U in the target sequence immediately 5' of the cleavage site.
Binds 4–6 nucleotides at the 5'-side of the cleavage site.
Reaction mechanism: attack by the 3'-OH of guanosine to generate cleavage products with 3'-OH and 5'-guanosine.
Additional protein cofactors required in some cases to help folding and maintenance of the active structure.
Over 300 known members of this class. Found as an intervening sequence in *Tetrahymena thermophila* rRNA, fungal mitochondria, chloroplasts, phage T4, blue-green algae, and others.
Major structural features largely established through phylogenetic comparisons, mutagenesis, and biochemical studies [$^i$,$^{ii}$].
Complete kinetic framework established for one ribozyme [$^{iii}$,$^{iv}$,$^v$,$^{vi}$].
Studies of ribozyme folding and substrate docking underway [$^{vii}$,$^{viii}$,$^{ix}$].
Chemical modification investigation of important residues well established [$^x$,$^{xi}$].
The small (4–6 nt) binding site may make this ribozyme too non-specific for targeted RNA cleavage, however, the Tetrahymena group I intron has been used to repair a "defective" β-galactosidase message by the ligation of new β-galactosidase sequences onto the defective message [$^{xii}$].

RNAse P RNA (M1 RNA)

Size: ~290 to 400 nucleotides.
RNA portion of a ubiquitous ribonucleoprotein enzyme.
Cleaves tRNA precursors to form mature tRNA [$^{xiii}$].
Reaction mechanism: possible attack by $M^{2+}$-OH to generate cleavage products with 3'-OH and 5'-phosphate.
RNAse P is found throughout the prokaryotes and eukaryotes. The RNA subunit has been sequenced from bacteria, yeast, rodents, and primates.
Recruitment of endogenous RNAse P for therapeutic applications is possible through hybridization of an External Guide Sequence (EGS) to the target RNA [$^{xiv}$,$^{xv}$]
Important phosphate and 2' OH contacts recently identified [$^{xvi}$,$^{xvii}$]

Group II Introns

Size: >1000 nucleotides.
Trans cleavage of target RNAs recently demonstrated [$^{xviii}$,$^{xix}$].
Sequence requirements not fully determined.
Reaction mechanism: 2'-OH of an internal adenosine generates cleavage products with 3'-OH and a "lariat" RNA containing a 3'–5' and a 2'–5' branch point.
Only natural ribozyme with demonstrated participation in DNA cleavage [$^{xx}$, $^{xxi}$] in addition to RNA cleavage and ligation.
Major structural features largely established through phylogenetic comparisons [$^{xxii}$].
Important 2' OH contacts beginning to be identified [$^{xxiii}$]
Kinetic framework under development [$^{xxiv}$]

Neurospora VS RNA

Size: ~144 nucleotides.
Trans cleavage of hairpin target RNAs recently demonstrated [$^{xxv}$].
Sequence requirements not fully determined.
Reaction mechanism: attack by 2'-OH 5' to the scissile bond to generate cleavage products with 2',3'-cyclic phosphate and 5'-OH ends.
Binding sites and structural requirements not fully determined.
Only 1 known member of this class. Found in Neurospora VS RNA.

TABLE I-continued

Characteristics of naturally occurring ribozymes

Hammerhead Ribozyme
(see text for references)

Size: ~13 to 40 nucleotides.
Requires the target sequence UH immediately 5' of the cleavage site.
Binds a variable number nucleotides on both sides of the cleavage site.
Reaction mechanism: attack by 2'-OH 5' to the scissile bond to generate cleavage products with 2',3'-cyclic phosphate and 5'-OH ends.
14 known members of this class. Found in a number of plant pathogens (virusoids) that use RNA as the infectious agent.
Essential structural features largely defined, including 2 crystal structures [xxvi, xxvii]
Minimal ligation activity demonstrated (for engineering through in vitro selection) [xxviii]
Complete kinetic framework established for two or more ribozymes [xxix].
Chemical modification investigation of important residues well established [xxx].

Hairpin Ribozyme

Size: ~50 nucleotides.
Requires the target sequence GUC immediately 3' of the cleavage site.
Binds 4–6 nucleotides at the 5'-side of the cleavage site and a variable number to the 3'-side of the cleavage site.
Reaction mechanism: attack by 2'-OH 5' to the scissile bond to generate cleavage products with 2',3'-cyclic phosphate and 5'-OH ends.
3 known members of this class. Found in three plant pathogen (satellite RNAs of the tobacco ringspot virus, arabis mosaic virus and chicory yellow mottle virus) which uses RNA as the infectious agent.
Essential structural features largely defined [xxxi, xxxii, xxxiii, xxxiv]
Ligation activity (in addition to cleavage activity) makes ribozyme amenable to engineering through in vitro selection [xxxv]
Complete kinetic framework established for one ribozyme [xxxvi].
Chemical modification investigation of important residues begun [xxxvii, xxxviii].

Hepatitis Delta Virus (HDV) Ribozyme

Size: ~60 nucleotides.
Trans cleavage of target RNAs demonstrated [xxxix].
Binding sites and structural requirements not fully determined, although no sequences 5' of cleavage site are required. Folded ribozyme contains a pseudoknot structure [xl].
Reaction mechanism: attack by 2'-OH 5' to the scissile bond to generate cleavage products with 2',3'-cyclic phosphate and 5'-OH ends.
O[xli]nly 2 known members of this class. Found in human HDV.
Circular form of HDV is active and shows increased nuclease stability [xlii]

---

[i]Michel, Francois; Westhof, Eric. Slippery substrates. Nat. Struct. Biol. (1994), 1(1), 5–7.
[ii]Lisacek, Frederique; Diaz, Yolande; Michel, Francois. Automatic identification of group I intron cores in genomic DNA sequences. J. Mol. Biol. (1994), 235(4), 1206–17.
[iii]Herschlag, Daniel; Cech, Thomas R.. Catalysis of RNA cleavage by the Tetrahymena thermophila ribozyme. 1. Kinetic description of the reaction of an RNA substrate complementary to the active site. Biochemistry (1990), 29(44), 10159–71.
[iv]Herschlag, Daniel; Cech, Thomas R.. Catalysis of RNA cleavage by the Tetrahymena thermophila ribozyme. 2. Kinetic description of the reaction of an RNA substrate that forms a mismatch at the active site. Biochemistry (1990), 29(44), 10172–80.
[v]Knitt, Deborah S.; Herschlag, Daniel. pH Dependencies of the Tetrahymena Ribozyme Reveal an Unconventional Origin of an Apparent pKa. Biochemistry (1996), 35(5), 1560–70.
[vi]Bevilacqua, Philip C.; Sugimoto, Naoki; Turner, Douglas H.. A mechanistic framework for the second step of splicing catalyzed by the Tetrahymena ribozyme. Biochemistry (1996), 35(2), 648–58.
[vii]Li, Yi; Bevilacqua, Philip C.,; Mathews, David; Turner, Douglas H.. Thermodynamic and activation parameters for binding of a pyrene-labeled substrate by the Tetrahymena ribozyme: docking is not diffusion-controlled and is driven by a favorable entropy change. Biochemistry (1995), 34(44), 14394–9.
[viii]Banerjee, Aloke Raj; Turner, Douglas H.. The time dependence of chemical modification reveals slow steps in the folding of a group I ribozyme. Biochemistry (1995), 34(19), 6504–12.
[ix]Zarrinkar, Patrick P.; Williamson, James R.. The P9.1-P9.2 peripheral extension helps guide folding of the Tetrahymena ribozyme. Nucleic Acids Res. (1996), 24(5), 854–8.
[x]Strobel, Scott A.; Cech, Thomas R.. Minor groove recognition of the conserved G.cntdot.U pair at the Tetrahymena ribozyme reaction site. Science (Washington, D. C.) (1995), 267(5198), 675–9.
[xi]Strobel, Scott A.; Cech, Thomas R.. Exocydic Amine of the Conserved G.cntdot.U Pair at the Cleavage Site of the Tetrahymena Ribozyme Contributes to 5'-Splice Site Selection and Transition State Stabilization. Biochemistry (1996), 35(4), 1201–11.
[xii]Sullenger, Bruce A.; Cech, Thomas R.. Ribozyme-mediated repair of defective mRNA by targeted trans-splicing. Nature (London) (1994), 371 (6498), 619–22.
[xiii]Robertson, H.D.; Altman, S.; Smith, J.D. J. Biol. Chem., 247, 5243–5251 (1972).
[xiv]Forster, Anthony C.; Altman Sidney. External guide sequences for an RNA enzyme. Science (Washington, D. C., 1883-) (1990), 249(4970), 783–6.
[xv]Yuan, Y.; Hwang, E. S.; Altman, S. Targeted cleavage of mRNA by human RNase P. Proc. Natl. Acad. Sci. USA (1992) 89, 8006–10.
[xvi]Harris, Michael E.; Pace, Norman R.. Identification of phosphates involved in catalysis by the ribozyme RNase P RNA. RNA (1995), 1(2), 210–18.
[xvii]Pan, Tao; Loria, Andrew; Zhong, Kun. Probing of tertiary interactions in RNA: 2'-hydroxyl-base contacts between the RNase P RNA and pre-tRNA. Proc. Natl. Acad. Sci. U. S. A. (1995), 92(26), 12510–14.
[xviii]Pyle, Anna Marie; Green, Justin B.. Building a Kinetic Framework for Group II Intron Ribozyme Activity: Quantitation of Interdomain Binding and Reaction Rate. Biochemistry (1994), 33(9), 2716–25.
[xix]Michels, William J. Jr.; Pyle, Anna Marie. Conversion of a Group II Intron into a New Multiple-Turnover Ribozyme that Selectively Cleaves Oligonucleotides: Elucidation of Reaction Mechanism and Structure/Function Relationships. Biochemistry (1995), 34(9), 2965–77.
[xx]Zimmerly, Steven; Guo, Huatao; Eskes, Robert; Yang, Jian; Perlman, Philip S.; Lambowitz, Alan M.. A group II intron RNA is a catalytic component of a DNA endonuclease involved in intron mobility. Cell (Cambridge, Mass.) (1995), 83(4), 529–38.
[xxi]Griffin, Edmund A., Jr.; Qin, Zhifeng; Michels, Williams J., Jr.; Pyle, Anna Marie. Group II intron ribozymes that cleave DNA and RNA linkages with similar efficiency, and lack contacts with substrate 2'-hydroxyl groups. Chem. Biol. (1995), 2(11), 761–70.
[xxii]Michel, Francois; Ferat, Jean Luc. Structure and activities of group II introns. Annu. Rev. Biochem. (1995), 64,435–61.
[xxiii]Abramovitz, Dana L.; Friedman, Richard A.; Pyle, Anna Marie. Catalytic role of 2'-hydroxyl groups within a group II intron active site. Science (Washington, D. C.) (1996), 271(5254), 1410–13.
[xxiv]Daniels, Danette L.; Michels, William J., Jr.; Pyle, Anna Marie. Two competing pathways for self-splicing by group II introns: a quantitative analysis of in vitro reaction rates and products. J. Mol. Biol. (1996), 256 (1), 31–49.
[xxv]Guo, Hans C. T.; Collins, Richard A.. Efficient trans-cleavage of a stem-loop RNA substrate by a ribozyme derived from Neurospora VS RNA. EMBO J. (1995), 14(2), 368–76.
[xxvi]Scott, W.G., Finch, J.T., Aaron,K. The crystal structure of an all RNA hammerhead ribozyme:Aproposed mechanism for RNA catalytic cleavage. Cell, (1995), 81, 991–1002.
[xxvii]McKay, Structure and function of the hammerhead ribozyme: an unfinished story. RNA, (1996), 2, 395–403.
[xxviii]Long, D., Uhlenbeck, O., Hertel, K. Ligation with hammerhead ribozymes. U.S. Pat. No. 5,633,133.
[xxix]Hertel, K.J., Herschlag, D., Uhlenbeck, O. A kinetic and thermodynamic framework for the hammerhead ribozyme reaction. Biochemistry, (1994) 33, 3374–3385.Beigelman, L., et al., Chemical modifications of hammerhead ribozymes. J. Biol. Chem., (1995) 270, 25702–25708.
[xxx]Beigelman, L., et al., Chemical modifications of hammerhead ribozymes. J. Biol. Chem., (1995) 270, 25702–25708.
[xxxi]Hampel, Arnold; Tritz, Richard; Hicks, Margaret; Cruz, Phillip. 'Hairpin' catalytic RNA model: evidence for helixes and sequence requirement for substrate RNA. Nucleic Acids Res. (1990), 18(2), 299–304.
[xxxii]Chowrira, Bharat M.; Berzal-Herranz, Alfredo; Burke, John M.. Novel guanosine requirement for catalysis by the hairpin ribozyme. Nature (London) (1991), 354(6351), 320–2.
[xxxiii]Berzal-Herranz, Alfredo; Joseph, Simpson; Chowrira, Bharat M.; Butcher, Samuel E.; Burke, John M.. Essential nucleotide sequences and secondary structure elements of the hairpin ribozyme. EMBO J. (1993), 12(6), 2567–73.
[xxxiv]Joseph, Simpson; Berzal-Herranz, Alfredo; Chowrira, Bharat M.; Butcher, Samuel E.. Substrate selection rules for the hairpin ribozyme determined by in vitro selection, mutation, and analysis of mismatched substrates. Genes Dev. (1993), 7(1), 130–8.
[xxxv]Berzal-Herranz, Alfredo; Joseph, Simpson; Burke, John M.. In vitro selection of active hairpin ribozymes by sequential RNA-catalyzed cleavage and ligation reactions. Genes Dev. (1992), 6(1), 129–34.

TABLE I-continued

Characteristics of naturally occurring ribozymes

[xxxvi]Hegg, Lisa A.; Fedor, Martha J.. Kinetics and Thermodynamics of Intermolecular Catalysis by Hairpin Ribozymes. Biochemistry (1995), 34(48), 15813–28.
[xxxvii]Grasby, Jane A.; Mersmann, Karin; Singh, Mohinder; Gait, Michael J.. Purine Functional Groups in Essential Residues of the Hairpin Ribozyme Required for Catalytic Cleavage of RNA. Biochemistry (1995), 34(12), 4068–76.
[xxxviii]Schmidt, Sabine; Beigelman, Leonid; Karpeisky, Alexander; Usman, Nassim; Sorensen, Ulrik S.; Gait, Michael J.. Base and sugar requirements for RNA cleavage of essential nucleoside residues in internal loop B of the hairpin ribozyme: implications for secondary structure. Nucleic Acids Res. (1996), 24(4), 573–81.
[xxxix]Perrotta, Anne T.; Been, Michael D.. Cleavage of oligoribonucleotides by a ribozyme derived from the hepatitis .delta. virus RNA sequence. Biochemistry (1992), 31(1), 16–21.
[xl]Perrotta, Anne T.; Been, Michael D.. A pseudoknot-like structure required for efficient self-cleavage of hepatitis delta virus RNA. Nature (London) (1991), 350(6317), 434–6.
[xli]
[xlii]Puttaraju, M.; Perrotta, Anne T.; Been, Michael D.. A circular trans-acting hepatitis delta virus ribozyme. Nucleic Acids Res. (1993), 21(18), 4253–8.

TABLE III

FLT GeneBloc sequences

Active GeneBloc, 3.1 chemistry $u_s g_s a_s uucuT_s T_s C_s C_s A_s G_s G_s C_s T_s caug_s a_s a_s T$ (SEQ ID NO: 1)

Mismatch control, 3.1 chemistry $u_s g_s a_s uucuT_s T_s G_s C_s C_s G_s A_s T_s caug_s a_s a_s T$ (SEQ ID NO: 2)

Active GeneBloc, 3.3 chemistry

B $ugauucuT_s T_s C_s C_s A_s G_s G_s C_s T_s caugaau$ B (SEQ ID NO: 3)

Mismatch control, 3.3 chemistry

B $ugauucuT_s T_s G_s C_s C_s G_s A_s T_s caugaau$ B (SEQ ID NO: 4)

lower case = 2'-OMethyl ribonucleotides

Upper case = deoxyribonucleotides (DNA)

s = phosphorothioate linkages

B = inverted deoxyabasic

TABLE II

A. 2.5 μmol Synthesis Cycle ABI 394 Instrument

| Reagent | Equivalents | Amount | Wait Time* DNA | Wait Time* 2'-O-methyl | Wait Time*RNA |
|---|---|---|---|---|---|
| Phosphoramidites | 6.5 | 163 μL | 45 sec | 2.5 min | 7.5 min |
| S-Ethyl Tetrazole | 23.8 | 238 μL | 45 sec | 2.5 min | 7.5 min |
| Acetic Anhydride | 100 | 233 μL | 5 sec | 5 sec | 5 sec |
| N-Methyl Imidazole | 186 | 233 μL | 5 sec | 5 sec | 5 sec |
| TCA | 176 | 2.3 mL | 21 sec | 21 sec | 21 sec |
| Iodine | 11.2 | 1.7 mL | 45 sec | 45 sec | 45 sec |
| Beaucage | 12.9 | 645 μL | 100 sec | 300 sec | 300 sec |
| Acetonitrile | NA | 6.67 mL | NA | NA | NA |

B. 0.2 μmol Synthesis Cycle ABI 394 Instrument

| Reagent | Equivalents | Amount | Wait Time* DNA | Wait Time* 2'-O-methyl | Wait Time*RNA |
|---|---|---|---|---|---|
| Phosphoramidites | 15 | 31 μL | 45 sec | 233 sec | 465 sec |
| S-Ethyl Tetrazole | 38.7 | 31 μL | 45 sec | 233 min | 465 sec |
| Acetic Anhydride | 655 | 124 μL | 5 sec | 5 sec | 5 sec |
| N-Methyl Imidazole | 1245 | 124 μL | 5 sec | 5 sec | 5 sec |
| TCA | 700 | 732 μL | 10 sec | 10 sec | 10 sec |
| Iodine | 20.6 | 244 μL | 15 sec | 15 sec | 15 sec |
| Beaucage | 7.7 | 232 μL | 100 sec | 300 sec | 300 sec |
| Acetonitrile | NA | 2.64 mL | NA | NA | NA |

C. 0.2 μmol Synthesis Cycle 96 well Instrument

| Reagent | Equivalents:DNA/ 2'-O-methyl/Ribo | Amount: DNA/2'-O-methyl/Ribo | Wait Time* DNA | Wait Time* 2'-O-methyl | Wait Time* Ribo |
|---|---|---|---|---|---|
| Phosphoramidites | 22/33/66 | 40/60/120 μL | 60 sec | 180 sec | 360 sec |
| S-Ethyl Tetrazole | 70/105/210 | 40/60/120 μL | 60 sec | 180 min | 360 sec |
| Acetic Anhydride | 265/265/265 | 50/50/50 μL | 10 sec | 10 sec | 10 sec |
| N-Methyl Imidazole | 502/502/502 | 50/50/50 μL | 10 sec | 10 sec | 10 sec |
| TCA | 238/475/475 | 250/500/500 μL | 15 sec | 15 sec | 15 sec |
| Iodine | 6.8/6.8/6.8 | 80/80/80 μL | 30 sec | 30 sec | 30 sec |
| Beaucage | 34/51/51 | 80/120/120 | 100 sec | 200 sec | 200 sec |
| Acetonitrile | NA | 1150/1150/1150 μL | NA | NA | NA |

*Wait time does not include contact time during delivery.

What is claimed is:

1. A nucleic acid molecule having the formula XIII:

wherein each r is independently a 2'-O-alkyl nucleotide, each D is independently a deoxyribonucleotide or 2'-arabinofluoro nucleotide, each s is independently a phosphorothioate, phosphorodithioate, 5'-thiophosphate, 3'-thiophosphate, or methylphosphonate internucleotide linkage, each p is independently a phosphodiester internucleotide linkage, and each iB is independently an inverted abasic moiety.

2. The nucleic acid molecule of claim 1, wherein said 2'-O-alkyl nucleotide is a 2'-O-methyl nucleotide.

3. The nucleic acid molecule of claim 1, wherein said 2'-O-alkyl nucleotide is a 2'-O-allyl nucleotide.

4. The nucleic acid molecule of claim 1, wherein said inverted abasic moiety is a 3',3'-linked or 5',5'-linked deoxyabasic moiety.

5. The nucleic acid molecule of claim 1, wherein said nucleic acid molecule is an antisense nucleic acid molecule.

6. The nucleic acid molecule of claim 1, wherein said nucleic acid molecule further comprises a 2–5A antisense chimera.

7. A method of modulating the expression of a gene in a cell in culture comprising the step of administering to said cell a nucleic acid molecule of claim 1 under conditions suitable for the down regulation of said gene.

8. A mammalian cell in culture including a nucleic acid molecule of claim 1.

9. The mammalian cell of claim 8, wherein said mammalian cell is a human cell.

10. A composition comprising the nucleic acid molecule of claim 1 and a pharmaceutically acceptable carrier.

11. A method of administering to a cell in culture a nucleic acid molecule of claim 1 comprising contacting said cell with the nucleic acid molecule under conditions suitable for said administration.

12. The method of claim 11, wherein said cell is a mammalian cell.

13. The method of claim 11, wherein said cell is a human cell.

14. The method of claim 11, wherein said administration is in the presence of a delivery reagent.

15. The method of claim 14, wherein said delivery reagent is a lipid.

16. The method of claim 15, wherein said lipid is a cationic lipid.

17. The method of claim 14, wherein said delivery reagent is a liposome.

* * * * *